US012491081B2

(12) United States Patent
Lillig et al.

(10) Patent No.: US 12,491,081 B2
(45) Date of Patent: Dec. 9, 2025

(54) SPINAL IMPLANT WITH FLEXIBLE SCREW LOCK MECHANISM

(71) Applicant: NuVasive, Inc., San Diego, CA (US)

(72) Inventors: Steven Lillig, San Diego, CA (US); Thomas Sweeney, San Diego, CA (US); Garrett Gleeson, San Diego, CA (US); Garrett Mikels, San Diego, CA (US); Logan McLennan, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 148 days.

(21) Appl. No.: 18/552,571

(22) PCT Filed: Apr. 3, 2022

(86) PCT No.: PCT/US2022/023224
§ 371 (c)(1),
(2) Date: Sep. 26, 2023

(87) PCT Pub. No.: WO2022/216566
PCT Pub. Date: Oct. 13, 2022

(65) Prior Publication Data

US 2024/0058136 A1 Feb. 22, 2024

Related U.S. Application Data

(60) Provisional application No. 63/188,277, filed on May 13, 2021, provisional application No. 63/170,531, filed on Apr. 4, 2021.

(51) Int. Cl.
*A61F 2/44* (2006.01)
*A61F 2/46* (2006.01)
*A61F 2/30* (2006.01)

(52) U.S. Cl.
CPC .......... *A61F 2/4455* (2013.01); *A61F 2/4611* (2013.01); *A61F 2002/30476* (2013.01)

(58) Field of Classification Search
CPC ............................... A61F 2/442; A61F 2/4455
USPC ........................................... 623/17.11, 17.16
See application file for complete search history.

(56) References Cited

U.S. PATENT DOCUMENTS

| | | | | |
|---|---|---|---|---|
| 8,740,983 | B1 * | 6/2014 | Arnold .................. | A61F 2/4611 623/17.16 |
| 8,840,668 | B1 | 9/2014 | Donahoe et al. | |
| 2008/0249575 | A1 * | 10/2008 | Waugh .................... | A61F 2/447 606/301 |
| 2011/0313528 | A1 | 12/2011 | Laubert et al. | |
| 2014/0288655 | A1 | 9/2014 | Parry et al. | |
| 2018/0325694 | A1 * | 11/2018 | Petersheim ............. | A61F 2/447 |

OTHER PUBLICATIONS

International Search Report and Written Opinion of the International Searching Authority, International Application No. PCT/US2022/023224, pp. 1-12, Aug. 10, 2022.

* cited by examiner

*Primary Examiner* — Eduardo C Robert
*Assistant Examiner* — Christina Negrellirodriguez

(57) ABSTRACT

The present disclosure includes bone screws, spinal implant, drivers, and their assemblies thereof for surgical procedures of the spine including but not limited to anterior lumbar interbody fusion (ALIF) procedures.

18 Claims, 27 Drawing Sheets

SECTION C-C

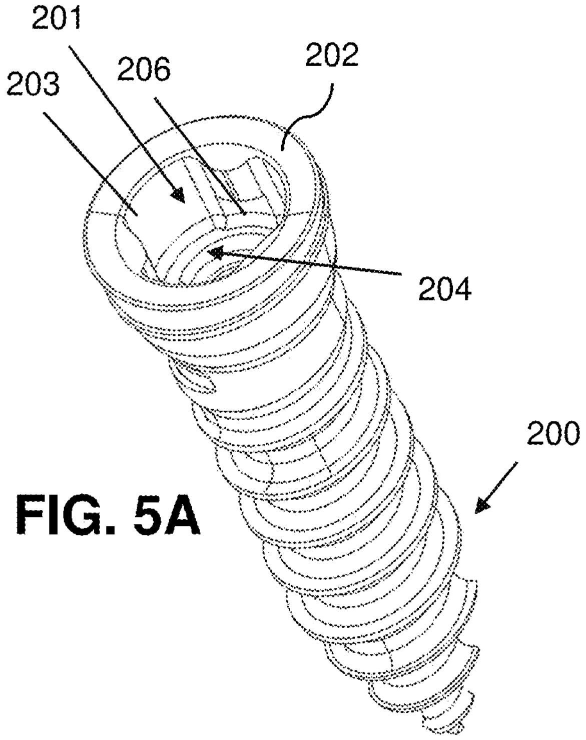
FIG. 5A
FIG. 5B
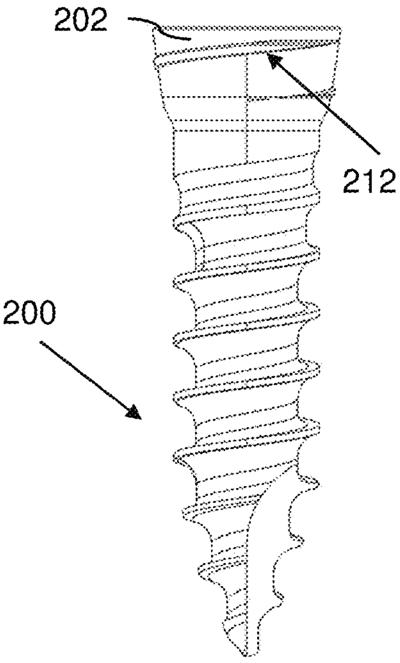
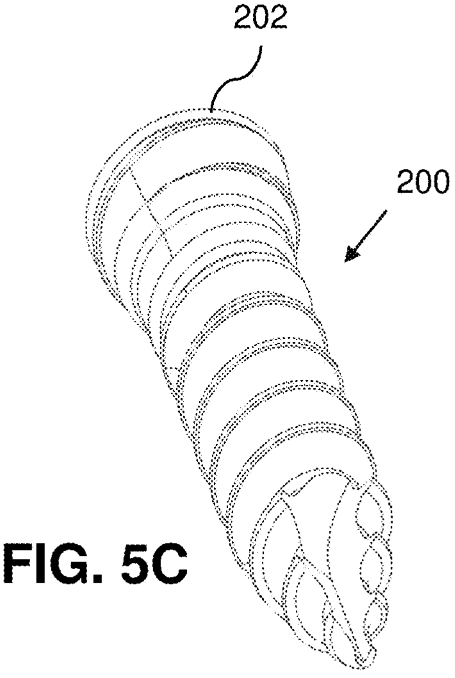
FIG. 5C
FIG. 5D
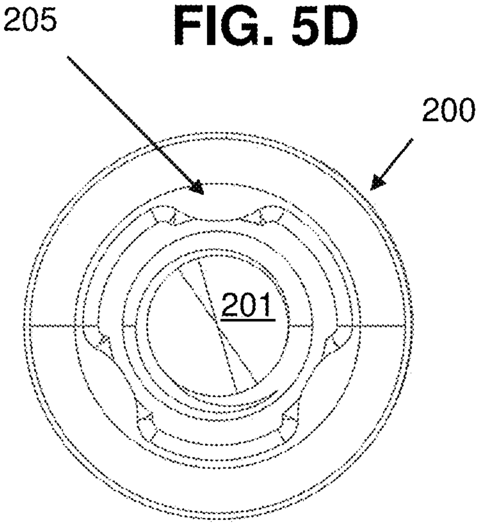

SPINAL IMPLANT WITH FLEXIBLE SCREW LOCK MECHANISM

CROSS REFERENCE TO RELATED APPLICATIONS

The present patent application claims the benefit of U.S. Provisional Patent Application No. 63/170,531, filed on Apr. 4, 2021; and U.S. Provisional Patent Application No. 63/188,277, filed on May 13, 2021. The foregoing applications are incorporated by reference as though fully set forth herein.

TECHNICAL FIELD

The present disclosure relates generally to bone screws, spinal implants, and instruments useful in spinal implant procedures, including inserters, trial inserters, screw drivers, and removal drivers for bone screws.

BACKGROUND OF THE DISCLOSURE

The spine is critical in human physiology for mobility, support, and balance. Spinal injuries can be debilitating or catastrophic to patients. Even small irregularities in the spine can cause devastating pain and loss of coordination.

Surgical procedures are commonly performed to correct problems with displaced, damaged, or degenerated intervertebral discs. Generally, spinal fusion procedures involve removing some or all of the diseased or damaged disc, and inserting one or more intervertebral implants into the resulting disc space. Successful replacement of injured or deteriorated spinal bone with artificial implants can involve consideration and understanding of the inherent stresses on the spine, as well as the biological properties of the body in response to the devices.

SUMMARY OF THE DISCLOSURE

In one aspect, disclosed herein is a spinal implant comprising: an upper endplate comprising a first plurality of micropores; a lower endplate comprising a second plurality of micropores; a central body fixedly placed between the upper and lower endplates, the central body comprising a plurality of pores formed by struts, a first and second end opposing each other, and two sides; and a plurality of fixation apertures, each of said plurality of fixation apertures defined by a solid wall and extending from the second end of the central body to one of the upper endplate or the lower endplate, wherein one or more of the solid walls includes a retaining feature configured to retain a bone screw within one or more of the plurality of fixation aperture and a confirmation feature configured to provide tactile feedback to a user when the bone screw has been fully inserted into the corresponding fixation aperture.

In some embodiments, the retaining feature is a passive retaining feature. In some embodiments, the retaining feature is a deflectable latch having a lip at a proximal end thereof and configured to allow passage of a bone screw in a first direction through the corresponding fixation aperture and retain the bone screw within the corresponding fixation aperture after a proximal portion of the bone screw has passed the lip. In some embodiments, the confirmation feature is a thread formed integrally as part of the solid wall and the bone screw further comprises a ridge on a proximal portion of the bone screw and wherein contact between the ridge and the thread provides tactile feedback to the user. In some embodiments, the solid wall defining each of the plurality of fixation apertures are not in contact with each other. In some embodiments, at least one of the solid walls defining a fixation aperture is in contact with at least one other solid wall defining a different fixation aperture. In some embodiments, at least one solid wall defining a fixation aperture is in contact with at least one of the struts in the central body. In some embodiments, the spinal implant further comprises an insertion tool engagement feature on the second end. In some embodiments, the insertion tool engagement feature is in contact with at least one of the solid walls defining a fixation aperture. In some embodiments, the insertion tool engagement feature is located between and in contact with at least two solid walls defining a fixation aperture. In some embodiments, one or more of the plurality of the fixation apertures extend from the second end to the upper endplate. In some embodiments, the lip of the deflectable latch extends at least towards the upper endplate. In some embodiments, one or more of the plurality of the fixation apertures extend from the second end to the lower endplate. In some embodiments, the lip of the deflectable latch extends at least towards the lower endplate. In some embodiments, the deflectable latch is integral to or fixedly attached to the solid wall. In some embodiments, the deflectable latch is fixedly attached to or integral to the central body. In some embodiments, the deflectable latch is solid. In some embodiments, the bone screw is configured to extend beyond the upper endplate and anchor in a first vertebral bone or extend beyond the lower endplate and anchor in a second vertebral bone. In some embodiments, the lip is configured to contact and hold the head of the bone screw in place thereby retaining the bone screw in the fully seated position. In some embodiments, the thread is at a distal portion of a corresponding fixation aperture. In some embodiments, the thread is a triple-lead thread. In some embodiments, the thread is configured to engage with a single ridge on the bone screw. In some embodiments, at least a portion of the spinal implant is 3D printed. In some embodiments, the spinal implant is 3D printed. In some embodiments, the spinal implant is made of titanium. In some embodiments, the plurality of pores of the central body comprises a first average pore size that is greater than an average pore size of the first plurality of micropores or an average pore size of the second plurality of micropores. In some embodiments, the insertion tool engagement feature is configured to engage a corresponding engagement feature of an inserter. In some embodiments, the engagement feature is not in contact with the solid walls of the plurality of fixation apertures. In some embodiments, the spinal implant further comprises a fusion aperture extending from the upper endplate to the lower endplate. In some embodiments, one or more of the plurality of fixation apertures extend in a first direction that is angled from the lower endplate by a first acute angle. In some embodiments, one or more the plurality of fixation apertures extends in a second direction that is angled from the lower endplate by a second acute angle. In some embodiments, the first end comprises a first height shorter than a second height of the second end.

In another aspect, disclosed herein is an inserter for inserting a spinal implant, the inserter comprising: an outer shaft comprising an elongate body containing a cavity therewithin and two opposing pins near a distal end of the elongate body, the two opposing pins extending inwardly from an inner surface of the elongate body; an inner shaft configured to be received in the cavity of the outer shaft, the inner shaft comprising a distal tip configured to be received in an engagement aperture of the spinal implant, and a barrel cam element near the distal tip, wherein the barrel cam element is configured to mate with the two opposing pins of the outer shaft; and a thumbwheel threadedly coupled to a proximal end of the inner shaft, wherein the thumbwheel is configured to rotate and cause rotation of the barrel cam element, thereby simultaneously rotating and translating the inner shaft relative to the outer shaft and the spinal implant.

In some embodiments, the simultaneous rotation and translation of the inner shaft is configured to couple the distal tip with the engagement aperture thereby locking or unlocking the inserter to the spinal implant. In some embodiments, the outer shaft further comprises two posts at the distal end of the elongate body, each of the two posts configured to mate with a side engagement slot of the spinal implant. In some embodiments, the two opposing pins are at or near a distal end of the barrel cam element in an unlocked position. In some embodiments, the two opposing pins are at or near a proximal end of the barrel cam element in a locked position.

In yet another aspect, disclosed herein is a driver for removing a bone screw from a spinal implant, the driver comprising: an outer sleeve containing a cavity therewithin; an inner shaft comprising a threaded distal end, the threaded distal end configured to couple with a threaded head of a bone screw thereby unthreading the bone screw from a spinal implant. The inner shaft is translatable at least distally relative to the outer sleeve through the cavity of the outer sleeve, and the outer sleeve is configured to deflect a deflectable latch latching on the thread head of the bone screw.

In some embodiments, the outer sleeve comprises a cannulated hexalobe drive feature at or near a distal end of the outer sleeve. In some embodiments, the threaded distal end of the inner shaft is disposed distally relative to a distal end of the outer sleeve. In some embodiments, the hexalobe drive feature is configured to couple to a corresponding feature of the threaded head of the bone screw to facilitate engagement to the bone screw. In some embodiments, the driver is configured to unlock the bone screw when a longitudinal axis of the bone screw is aligned with a longitudinal axis of the driver. In some embodiments, the driver is configured to unlock the bone screw when a longitudinal axis of the bone screw is angled away from a longitudinal axis of the driver. In some embodiments, the inner shaft further comprises a knob at a proximal end thereof, the knob is rotatable by the user thereby causing rotation of the inner shaft.

In yet another aspect, disclosed herein is a driver for removing a bone screw from a spinal implant, the driver comprising: a distal portion having a distal end; a drive feature proximal to the distal end, the drive feature configured to couple to a corresponding feature of a head of the bone screw to facilitate engagement to the bone screw; and a cam surface proximal to the drive feature. The cam surface is configured to deflect a deflectable latch of a spinal implant latching on the head of the bone screw outwardly thereby moving the deflectable latch out of a way of the bone screw.

In some embodiments, the distal end is narrower than the drive feature. In some embodiments, the drive feature comprises a trilobe. In some embodiments, the trilobe is configured to rotate and couple to an undercut of the corresponding feature of the head of the bone screw. In some embodiments, the driver further comprises an engagement feature configured to attach the distal portion to a handle. In some embodiments, the cam surf ace is located at least circumferentially on an outer surface of the distal portion.

In yet another aspect, disclosed herein is a driver for inserting a bone screw into a spinal implant, the driver comprising: an elongate body having a distal portion; a distal end; a drive feature located on an outer surface of the driver proximal to the distal end, the drive feature configured to couple to a corresponding feature of a head of the bone screw to facilitate engagement to the bone screw; and a flexible tab extending toward the distal end, the flexible tab configured to bias outwardly to retain the bone screw on the driver when the bone screw is loaded on the driver for insertion.

In some embodiments, the flexible tab comprises metal or alloy. In some embodiments, the flexible tab is positioned at least partly within a groove on the outer surface of the driver. In some embodiments, the drive feature comprises a corresponding trilobe feature distributed evenly around a circumference of the distal portion. In some embodiments, the drive feature comprises three grooves separating adjacent lobes of the trilobe feature. In some embodiments, the flexible tab is positioned at least partly within one of the three grooves. In some embodiments, the flexible tab is configured to move inwardly when loading the bone screw onto the driver. In some embodiments, the flexible tab, at its resting state, sits radially outward relative to an outer surface of the driver. In some embodiments, the flexible tab includes a proximal portion that is thicker than a distal portion thereof. In some embodiments, at least a part of the flexible tab is fixedly anchored to the elongate body of driver. In some embodiments, distal end is narrower than the drive feature. In some embodiments, the corresponding feature of the head of the bone screw includes a trilobe feature. In some embodiments, the trilobe feature is compatible with a driver with a hexalobe drive feature.

These and other aspects, advantages and salient features of the invention will become apparent from the following detailed description, which, when taken in conjunction with the annexed drawings, where like parts are designated by like reference characters throughout the drawings, disclose embodiments of the invention.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 5A-5D show various views of a bone screw as disclosed herein, in accordance with embodiments of the invention;

Figure 1:
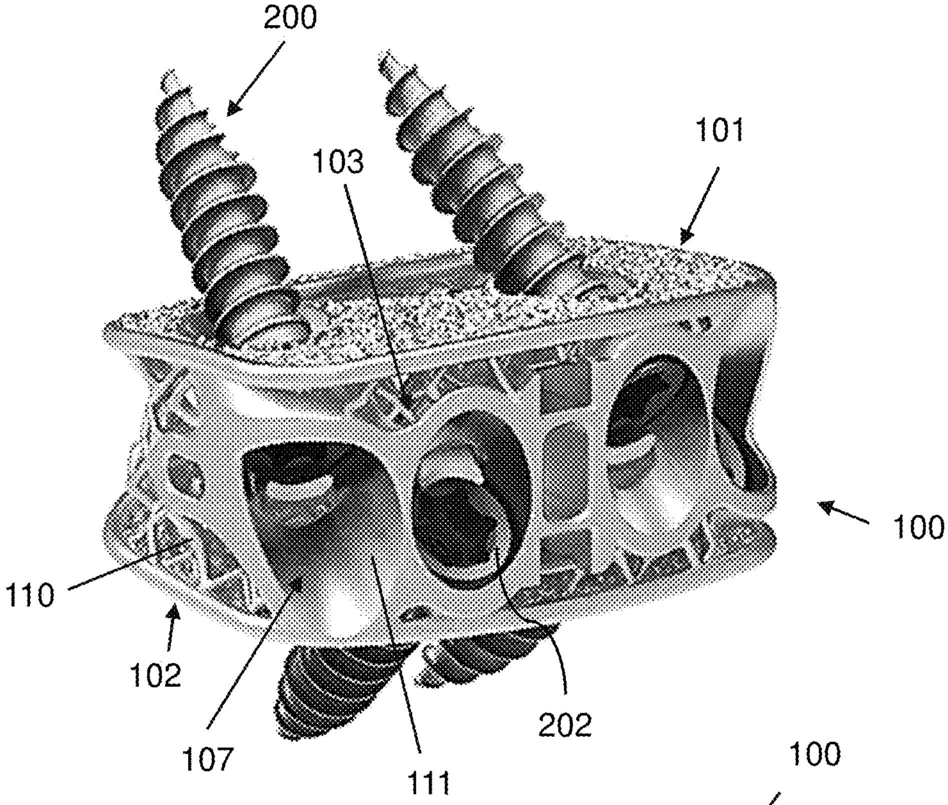
FIG. 1 shows a perspective view of a spinal implant with multiple bone screws in their locked or fully seated positions, in accordance with an embodiment of the invention.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings.

DETAILED DESCRIPTION OF THE DISCLOSURE

Overview

As disclosed herein, the term “bone screw” is interchangeable with or equivalent to the terms, “bone anchor,” “bone fastener,” “fixation screw,” and simply “screw”. An "interbody" is interchangeable with or equivalent to a "spinal implant," "fusion device," "implant," or "fusion implant" as used herein.

As disclosed herein, "proximal direction" indicates the direction away from attachment of an element to the subject, while "distal direction" indicates the direction opposite the proximal direction and toward attachment of an element to the subject.

In some embodiments, the bone screws, spinal implants or other devices are made of one or more biocompatible materials including, but not limited to, titanium, stainless steel, cobalt chrome, ceramics and/or thermoplastic materials.

Existing spinal implants, also referred to herein as interbodies, may be manufactured using additive manufacturing, or 3D printing processes, and may be made of titanium. Such interbodies may utilize a threaded connection to an inserter instrument. The threading can lead to inserters sticking to interbodies in situ and becoming difficult to remove. However, the lagging effect of a thread may be desirable as it eliminates toggle between the inserter and interbody or implant. Implants and instruments, including inserters, which address these and other challenges are described herein.

Spinal Implants

Disclosed herein are spinal implants, also referred to as fusion devices, interbodies, or fusion implants.

In some embodiments, the spinal implant is a 3D printed implant that requires no post machining. It can advantageously include a passive locking mechanism that deflects out of the way as the screw passes it during insertion. After traveling past the deflected latch, a small thread on the head of the screw can engage with a corresponding thread, e.g., a printed triple-lead thread, within the screw pocket to provide tactile feedback when the screw is past the latch and fully seated. The latch can spring back over the head of the screw to prevent screw back out should it loosen from the threads in the screw hole.

In some embodiments, the spinal implant advantageously includes a spring finger feature or latch that deflects out of the way during screw insertion and springs back capturing the head of the screw to keep it retained. The feature may be 3D printed or machined in.

The spinal implants disclosed herein advantageously provide a one step locking mechanism during screw insertion. Existing locking mechanisms have used springs but they are traditionally a separate piece from the implant. Other locking mechanisms may require a secondary step such as cam locks, additional cover plates, splaying of interfering component, etc. The locking deflectable latch disclosed herein requires no additional device or lock steps. The locking latch can be 3D printed into the implant with no post machining, which allows for small but complex geometries that were previously unattainable.

With reference to FIGS. 1, 2A-2G, and 3A-3D, the spinal implant 100 disclosed herein includes an upper endplate 101 comprising a first plurality of micropores; a lower endplate 102 comprising a second plurality of micropores; and a central body 103. Central body 103 may be fixedly placed between the upper and lower endplates 101, 102 or may be integral to the upper and lower endplates 101, 102. The central body 103 may include a plurality of pores formed by struts 110. The central body 103 may include a first and second end 104, 105 opposing each other (FIG. 2E), two sides 106, and a plurality of fixation apertures 107 (FIG. 2A) extending from the second end 105 of the central body 103 to either the upper endplate 101 or the lower endplate 102.

In the embodiment illustrated in the figures, the number of fixation apertures 107 is four, although other configurations are contemplated as would be understood by one of skill in the art. Two of the fixation apertures 107 are angled toward upper endplate 101, while two of the fixation apertures 107 are angled downward toward lower endplate 102.

Each fixation aperture 107 may include a solid wall 111 surrounding each aperture 107. One or more solid walls 111 can include a retaining feature configured to retain a bone screw 200 (FIG. 1) within one or more of the plurality of fixation aperture 107. In some embodiments, the retaining feature is passive. For example, as shown in FIG. 2D, the retaining feature is a deflectable latch 108 having a lip 109 at a proximal end thereof.

Figure 2A:
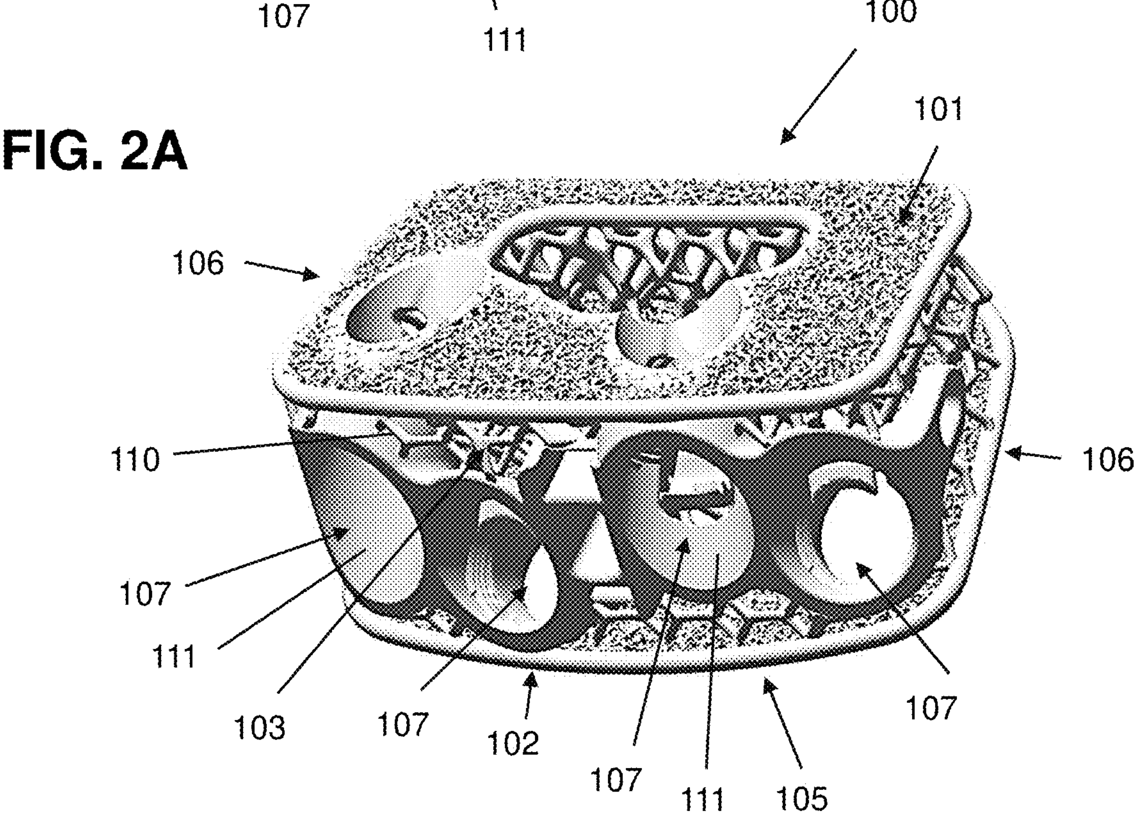
FIGS. 2A and 2B show perspective views of the spinal implant in FIG. 1, in accordance with the embodiments herein.
Figure 2B:
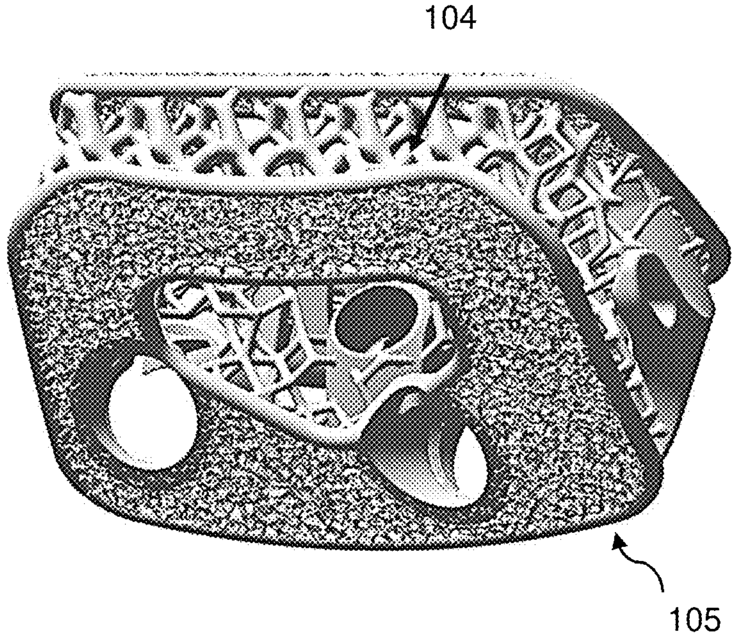
Figure 2C:
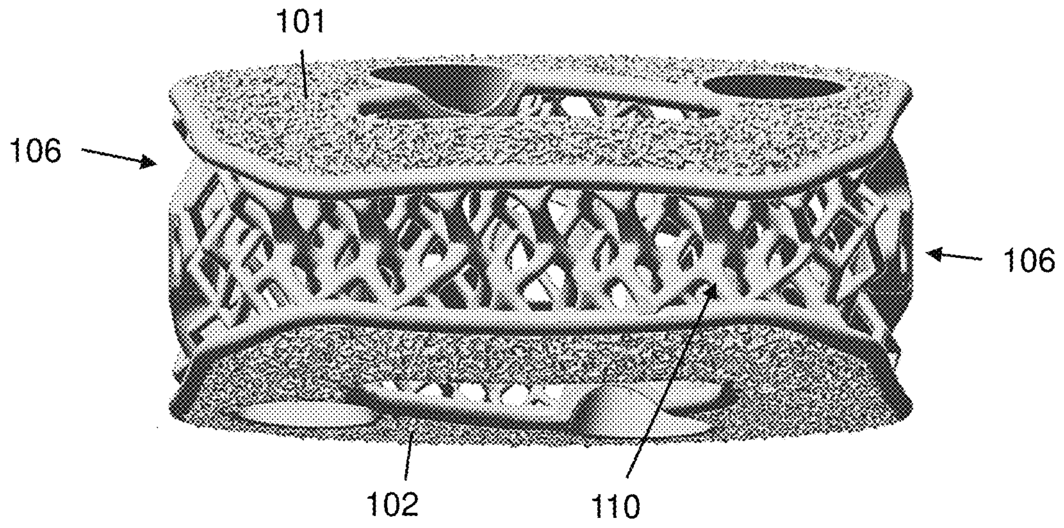
FIGS. 2C and 2D show posterior and anterior views of the spinal implant of FIG. 1 in accordance with an embodiment of the invention.
Figure 2D:
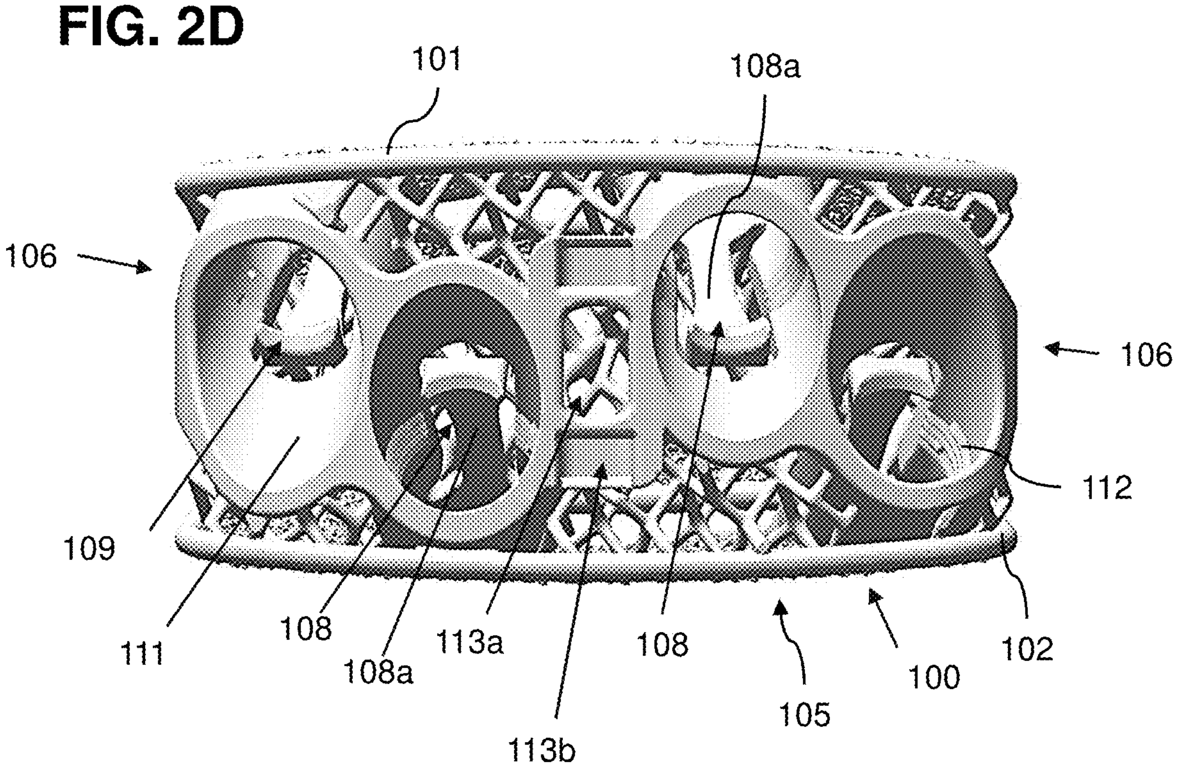
Figure 2E:
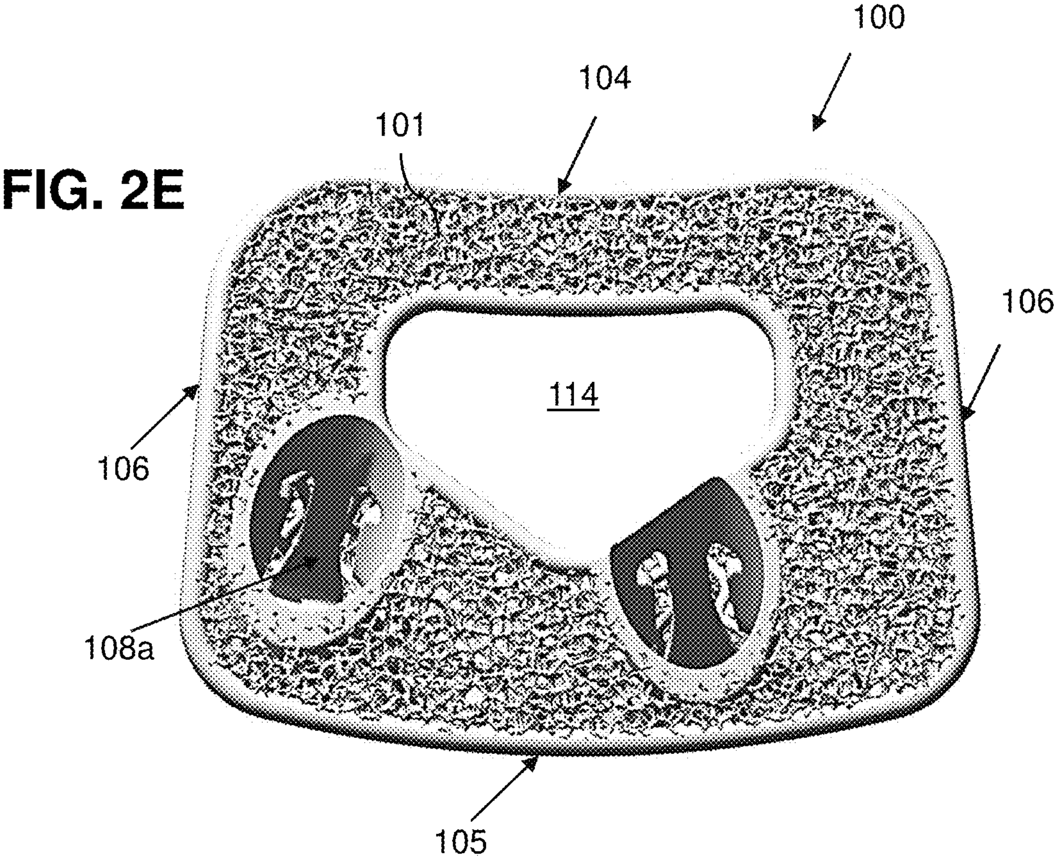
FIG. 2E shows a top view of the spinal implant of FIG. 1, in accordance with an embodiment of the invention.

Solid walls 111 may further include a confirmation feature configured to provide tactile feedback to a user when the bone screw 200 has been fully inserted into the corresponding fixation aperture 107. In some embodiments, the confirmation feature is a thread 112 formed integrally as part of the solid wall 111 (FIG. 2G). Bone screw 200 may further comprise a ridge 212 (FIG. 5B) disposed on a proximal portion, e.g., the head 202, of the bone screw 200. Contact between the ridge 212 and the thread 112 (FIG. 2G) provide tactile feedback to the user. In some embodiments, the deflectable latch 108 is configured to deflect and provide tactile feedback when a bone screw 200 passes the lip 109 and retains the bone screw 200 in a fully seated position after a head of the bone screw 200 passes the lip 109.

In some embodiments, the solid walls 111 defining each of the plurality of fixation apertures 107 are independent and have no contact with any of the other solid walls 111 defining other fixation apertures 107. In other embodiments, at least one of the solid walls 111 defining a fixation aperture 107 is in contact with at least one other solid wall 111 defining a different fixation aperture 107 (e.g., FIGS. 2A, 2D). In some embodiments, at least one solid wall 111 defining a fixation aperture 107 is in contact with at least one of the struts 110 in the central body 103.

As depicted in FIG. 1, spinal fusion implant 100 may include multiple fixation apertures 107, each with a deflectable latch 108 that is integral to the enclosure of the aperture 107. In this particular embodiment, multiple bone screws 200, e.g., four bone screws 200 (FIG. 1), are secured and fully seated in respective fixation apertures 107, and locked in place by deflectable latch 108, shown in FIG. 2D. The lip 109 at the proximal end of deflectable latch 108 securely holds head 202 of bone screw 200, thereby preventing backing out of bone screw 200 from the fully seated position as shown in FIG. 1. In this embodiment, one or more bone screws 200 are anchored in a first vertebra disposed superior to the implant 100, and one or more of bone screws 200 are anchored in a second vertebra disposed inferior to the implant 100. In certain embodiments, two bone screws 200 may be anchored in a first vertebra disposed superior to the implant 100, and two bone screws 200 are anchored in a second vertebra disposed inferior to the implant 100. The first and second vertebrae may or may not be adjacent to each other.

In some embodiments, one or more fixation apertures 107 comprise a solid wall 111 surrounding at least part of a corresponding fixation aperture 107. The deflectable latch 108 may be integral to or fixedly attached to the solid wall 111. The wall 111 may be made of a non-porous material. As discussed above, the wall 111 may include discontinuities near the deflectable latch 108 so that the latch 108 may move relative to the wall 111 and the rest of the implant 100. In some embodiments, one or more fixation apertures 107 may extend from the second end 105 to or through the upper end plate 101, and the lip 109 of the deflectable latch 108 associated with such fixation apertures 107 may extend at least toward the upper endplate 101. The fixation apertures 107 can extend from the second end 105 to and/or through the lower endplate 102. The lip 109 of the deflectable latch 108 may extend at least towards the lower endplate 102.

In some embodiments, one or more fixation apertures 107 extend in a first direction that is angled from the lower endplate 102 by a first acute angle, while other fixation aperture(s) extend in a second direction that is angled from the lower end plate 102 by a second acute angle.

The deflectable latch 108 may include an elongate flake 108*a* (FIGS. 2D, 2E) with a lip 109 at the proximal end of the flake 108*a*. The lip 109 of the deflectable latch 108, e.g., of elongate flake 108*a*, may extend at least towards the upper endplate 101. The distal end of the flake 108*a* may be fixedly attached to, or formed integrally with wall 111 of the aperture 107. As the wall 111 is integral to the central body 103 of the implant, the deflectable latch 108 is fixedly attached to or integral to the central body 103. The deflectable latch 108 may comprise a solid or non-porous material.

Figure 2F:
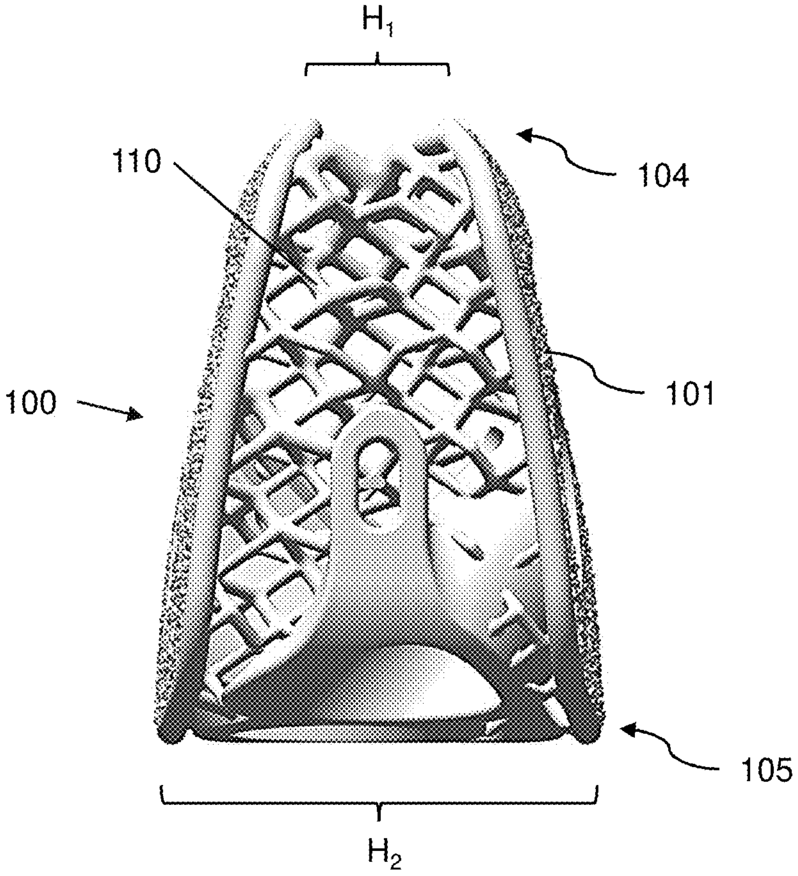
FIG. 2F shows a side view of the spinal implant of FIG. 1, in accordance with an embodiment of the invention.
Figure 2G:
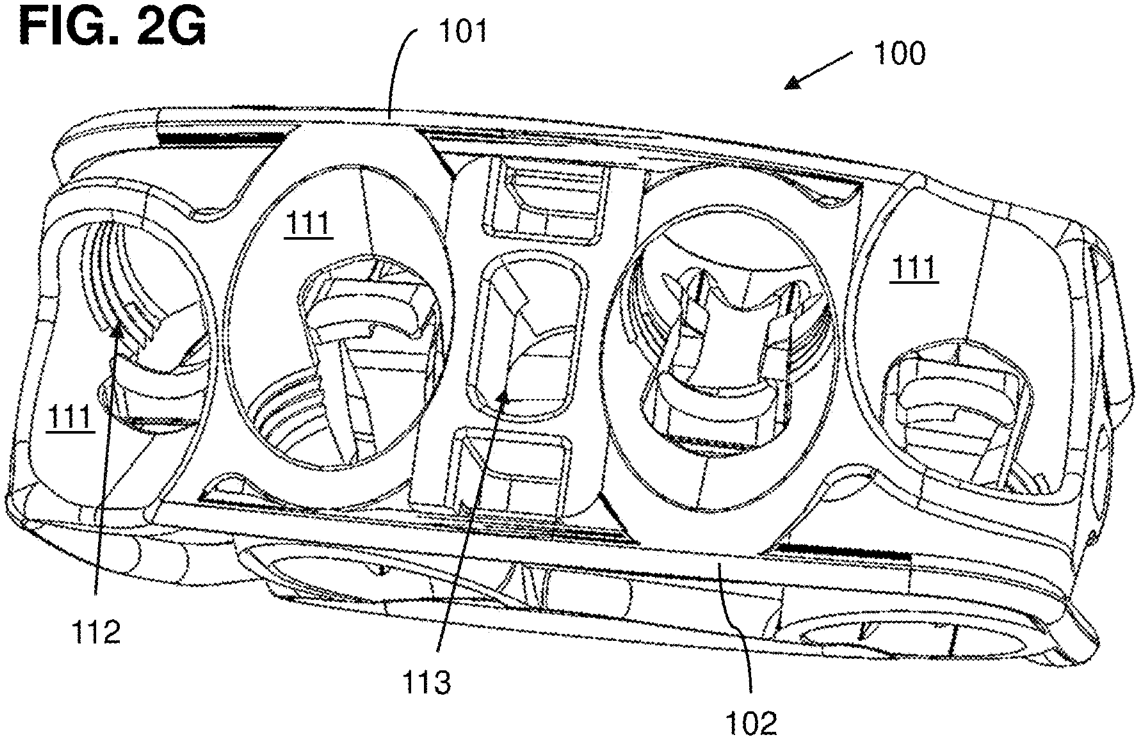
FIG. 2G shows a perspective view of the frame of the spinal implant of FIG. 1 without the porous structure, in accordance with an embodiment of the invention.
Figure 3A:
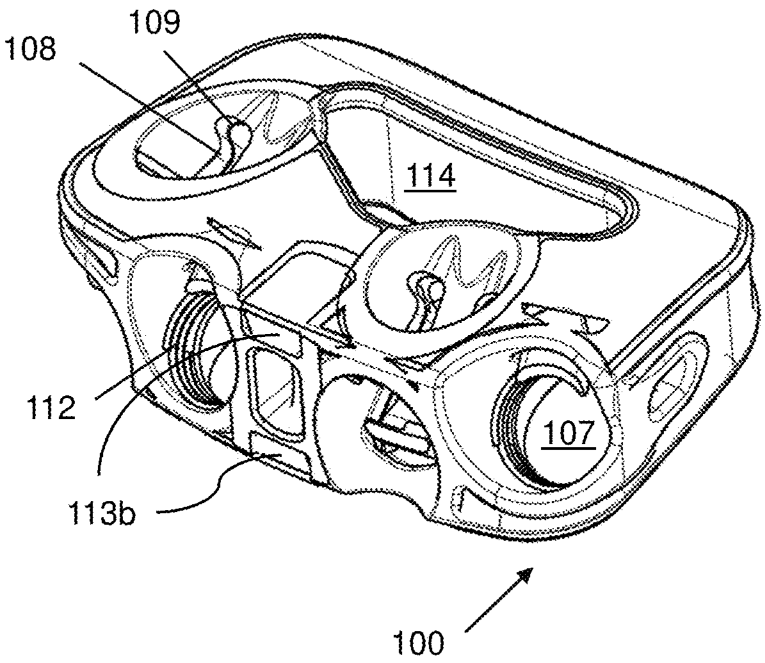
FIG. 3A shows a perspective view of a spinal implant, in accordance with an embodiment of the invention.
Figure 3B:
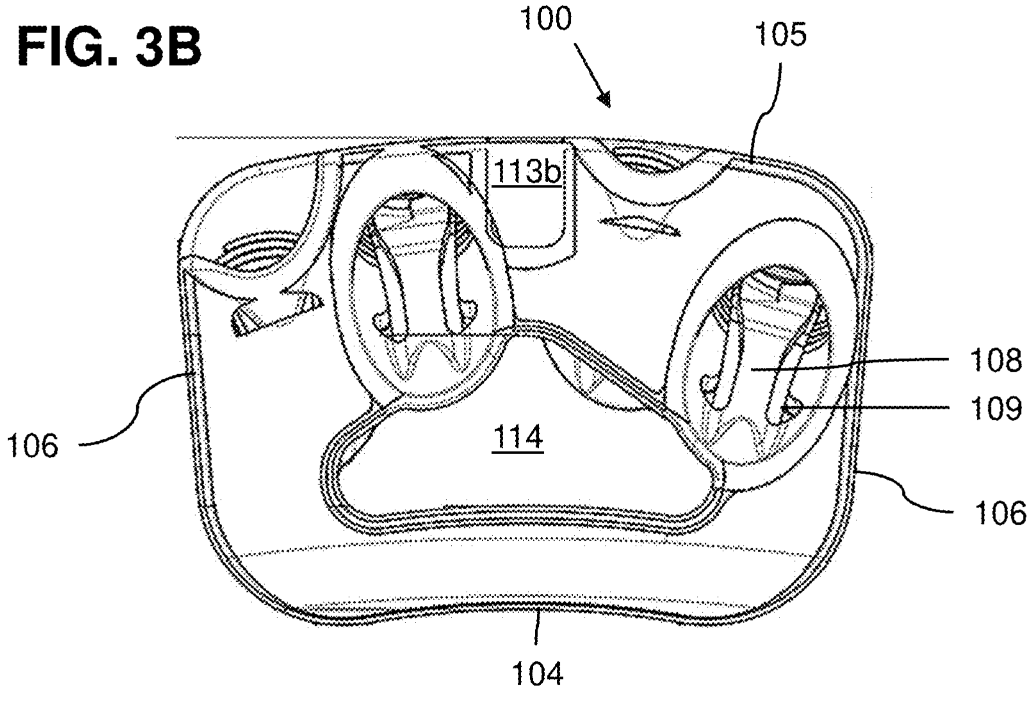
FIG. 3B shows a top view of a spinal implant, in accordance with an embodiment of the invention.
Figure 3C:
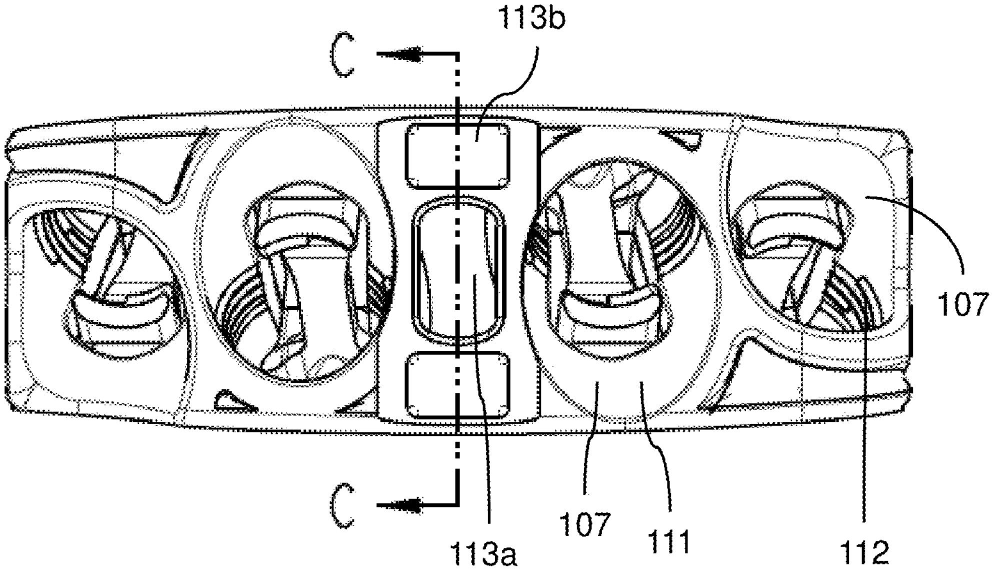
FIG. 3C shows an anterior view of a spinal implant, in accordance with an embodiment of the invention.
Figure 3D:
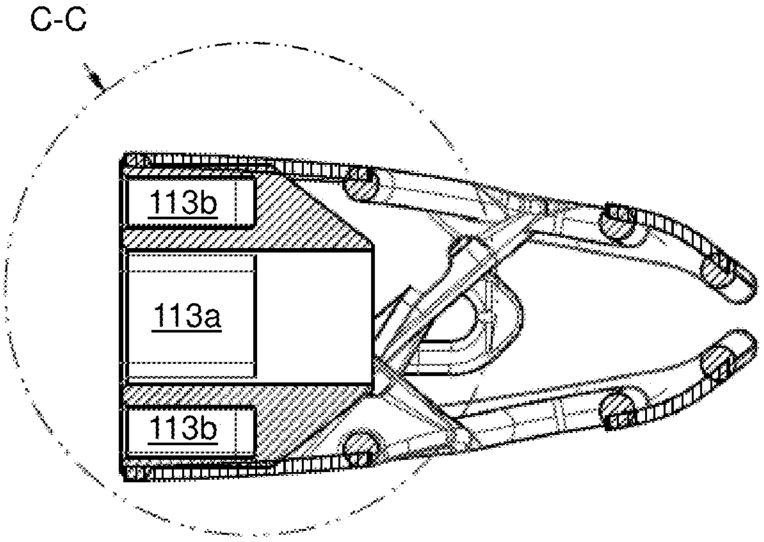
FIG. 3D shows a cross-sectional view of a spinal implant cutting at section line C-C in FIG. 3C, in accordance with an embodiment of the invention.

With reference to FIG. 2F, in some embodiments, the first end 104, which may be a posterior end in use, comprises a first, posterior height, $H_1$. Second end 105, which may be an anterior end in use, comprises a second, anterior height, $H_2$. In certain embodiments, posterior height $H_1$ of first end 104 may be smaller or shorter than anterior height $H_2$ of second end 105. In certain embodiments, posterior height $H_1$ of first end 104 may be, e.g., 6 mm, 8 mm, 10 mm, or 12 mm. The relationship of posterior height $H_1$ to anterior height $H_2$ may result in any of a number of lordotic options, including, e.g., 10°, 15°, 20°, 25°, and 30°.

In some embodiments, the bone screws 200 disclosed herein may, when fully inserted, extend beyond the upper end plate 101 and may anchor in a first vertebral bone or extend beyond the lower end plate 102 and anchor in a second vertebral bone. The lip 109 of the deflectable latch 108 contacts and holds a head 202 of the bone screw 200 in place, thereby retaining the bone screw 200 in the fully seated position, as can be seen in FIG. 1. Each of the plurality of fixation apertures 107 may include a thread 112 (FIGS. 2D, 2G) disposed on an inner circumferential surface of wall 111. Thread 112 may be configured to provide tactile feedback to a user when a bone screw 200 is inserted into a corresponding fixation aperture 107. The thread 112 may particularly be disposed in a distal portion of the corresponding fixation aperture 107, as shown in FIG. 2G. As a non-limiting example, the thread 112 may be, e.g., a triple-lead thread. The thread 112 may further be configured to engage with a single ridge 212 on the bone screw 200. Details of bone screw 200 are illustrated in FIGS. 5A-5D, with the ridge 212 best shown in FIG. 5B.

In some embodiments, at least a portion of the spinal implant 100 may be formed using additive manufacturing, i.e., implant 100 may be 3D printed. In some embodiments, the entirety of the spinal implant may be 3D printed. In some embodiment, at least a part of spinal implant 100 or the entirety of spinal implant 100 may be made of titanium.

Central body 103 (FIGS. 1, 2A) may comprise a plurality of pores, which may have an average pore size, e.g., a first average pore size. Upper endplate 101 and lower endplate 102 may also each have an average pore size, which may be a second average pore size and a third average pore size, respectively. In certain embodiments, the first average pore size of the pores in central body 103 may be greater than the second and the third average pore sizes of the pores in upper endplate 101 and lower endplate 102. Thus, the central body 103 may include micropores that are larger than micropores that may be present in the upper endplate 101 and/or the lower endplate 102, as can be seen in, e.g., FIGS. 2A-2C.

In some embodiments, implant 100 may further include a fusion aperture 114 extending from the upper end plate 101 to the lower end plate 102. Fusion implant 114 is shown in, e.g., FIGS. 2E, 3A, and 3B. Where implant 100 is placed between, e.g., the L5 and S1 vertebrae in patient, fusion of the L5 and S1 may occur via fusion aperture 114.

With reference to FIG. 2D, in some embodiments, spinal implant 100 may include an engagement aperture 113*a*, and a pair of engagement slots 113*b* at the second end 105. Engagement aperture 113*a* may be configured to receive and engage a corresponding and complementary sized and shaped engagement feature 312 of an inserter 300 (FIGS. 4G-4H), described further herein, while engagement slots 113*b* may be configured to receive and engage a pair of opposing posts 304, disposed on a distal end of inserter 300. Engagement aperture 113 may be configured to receive engagement feature 312 when engagement feature 312 is in a first orientation, and may include an undercut preventing withdrawal of engagement feature 312 from engagement aperture 113*a* after engagement feature 312 has rotated a certain amount, e.g., about 90°. In some embodiments, engagement aperture 113*a* may be substantially oblong in shape.

Engagement aperture 113*a* may be in contact with at least one of the solid walls 111 defining a fixation aperture 107. The engagement aperture 113*a* may be located between two solid walls 111 each defining a fixation aperture 107. In some embodiments, the engagement aperture 113*a*, e.g., the wall of the engagement aperture 113*a*, or at least part of the wall, may be located between and in contact with at least two solid walls 111, each defining a fixation aperture 107. In some embodiments, the engagement aperture 113*a* is located at or near a medial line of the implant 100, thus having an approximately equal distance to the two sides 106 of the implant 100.

Implant Inserters

As mentioned above, disclosed herein are inserters 300 configured for inserting the spinal fusion 100 implant into position in a patient.

With reference to FIGS. 4A-4G generally, inserter 300 includes an outer shaft 301 having an elongate body with a cavity or lumen disposed therein, and an inner shaft 310 disposed within the cavity in outer shaft 301. A proximal end of outer shaft 301 is coupled to a handle to aid in manipulating the device.

Outer shaft 301 may include a pair of opposing pins 303 disposed therein, near a distal end of elongate body 302. Opposing pins 303 may extend radially inwardly from an inner surface of elongate body 302, and are configured to mate with a barrel-cam style slot 313 (FIG. 4G) in the inner shaft 310 to simultaneously rotate and translate the inner shaft 310 with a single input. A threaded thumbwheel 320, disposed at a proximal end of inner shaft 310 and coupled thereto, may be used to provide the input. The two opposing pins 303 may be disposed at or near a distal end of barrel cam slot 313 in an unlocked position. The two opposing pins 303 can be at or near a proximal end of barrel cam slot 313 in a locked position.

Engagement feature 312 may be disposed at a distal end 311 of inner shaft 310. Engagement feature 312 is configured to be inserted into engagement aperture 113*a* on implant 100 in a keyed arrangement. After insertion of engagement feature 312 into engagement aperture 113*a*, thumbwheel 320 is turned to lag and retain implant 100. The inserters 300 disclosed herein can accomplish this motion with a slim profile which enables a medial attachment point to implant 100. This slim profile further facilitates the insertion or removal of screws 200 using drivers 500 and 400, respectively, while inserter 300 remains engaged with implant 100.

In some embodiments, the inserters 300 herein utilize a barrel-cam style mechanism to translate and rotate the inner shaft 310 with one input. The design achieves the lagging effect of a thread without utilizing a thread—in connection. The inserters 300 disclosed herein advantageously achieve the lagging effect without using the thread. The inserters 300 disclosed herein advantageously remove the problem of sticking (e.g., cold-welding) of inserter 300 and interbody 100 interface in-situ. In addition, existing 3D printed titanium interbodies 100 may require post-machining of a threaded inserter feature after the printing process. Eliminating the thread from the interbody 100 reduces steps in the process.

Thumbwheel 320 may be threadedly coupled to a proximal end of the inner shaft 310. As described herein, thumbwheel 320 may be configured to rotate and to cause rotation of the barrel cam element 313, thereby causing simultaneous rotating and translating of the inner shaft 310 relative to the outer shaft 302 and the spinal implant 100. In some embodiments, rotation of the thumb wheel 320 may cause simultaneous rotation and translation of the inner shaft 310 relative to the outer shaft 302 and may cause coupling or uncoupling of the distal tip 311 and engagement feature 312 of the inner shaft 310 with the engagement aperture 113*a* of the implant 100, thereby locking or unlocking the inserter 300 to or from the spinal implant 100.

Figure 4A:
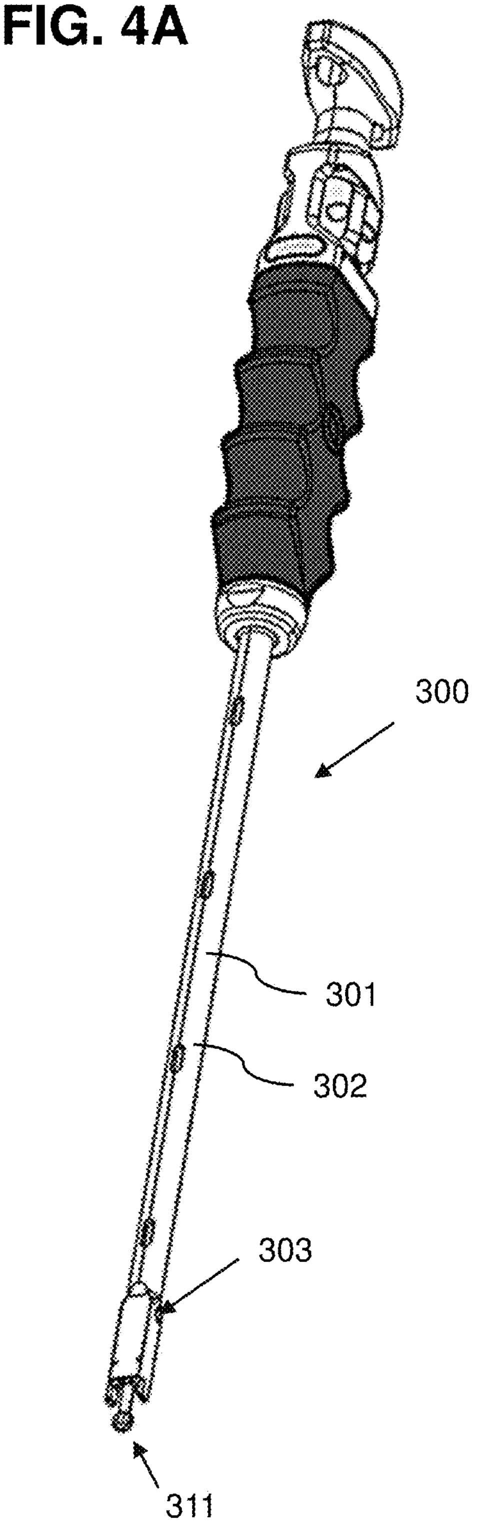
FIGS. 4A-4F show various views of an inserter as disclosed herein, in accordance with an embodiment of the invention.
Figure 4B:
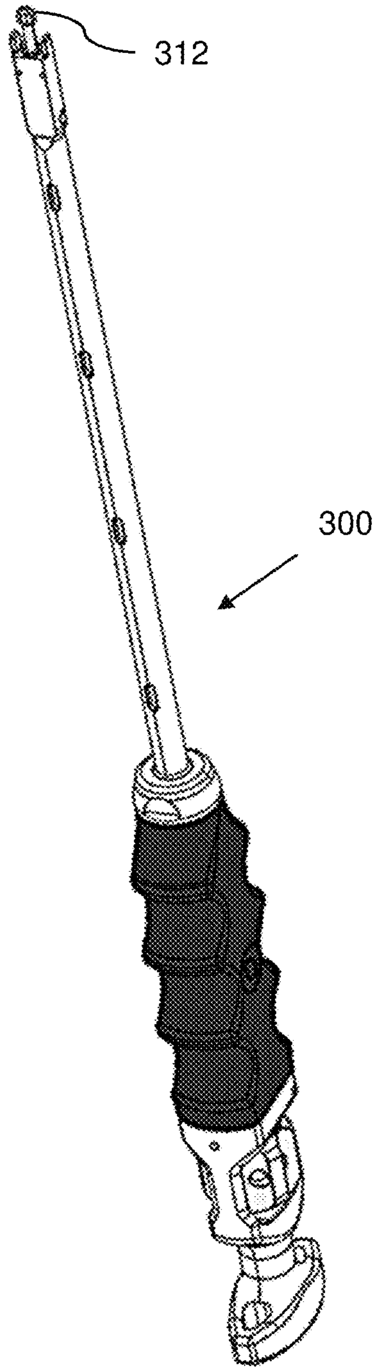
Figure 4C:
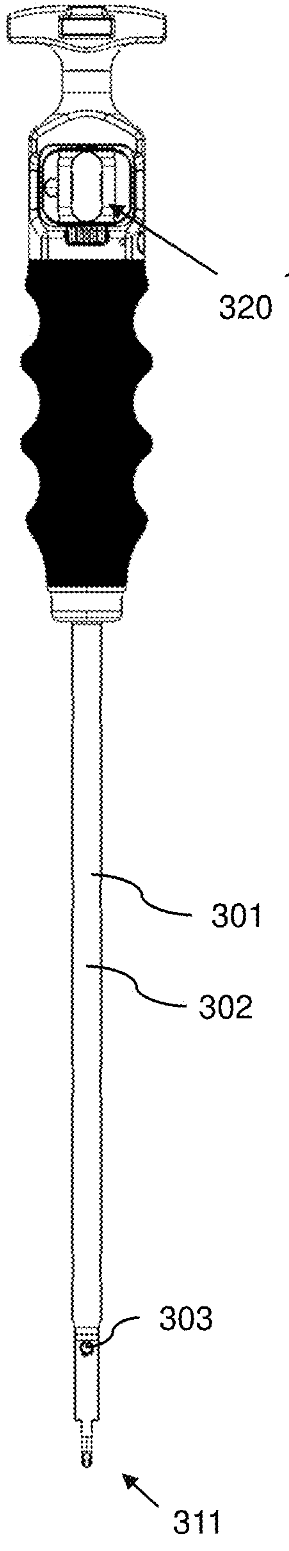
Figure 4D:
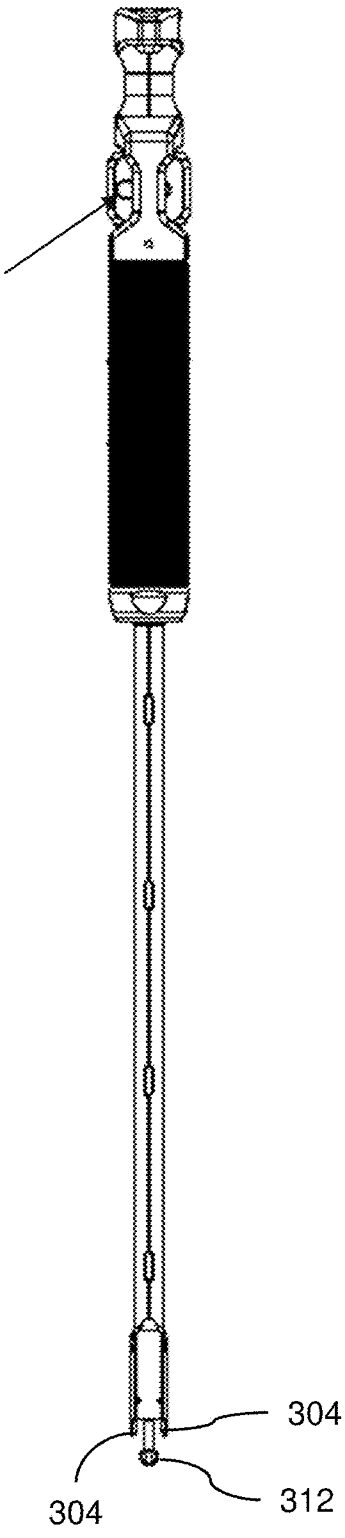
Figure 4E:
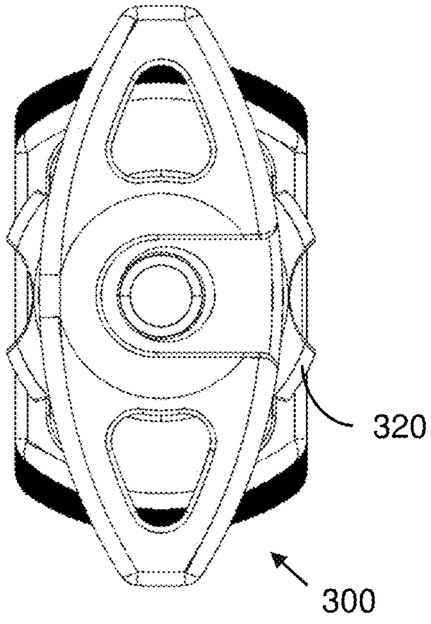
Figure 4F:
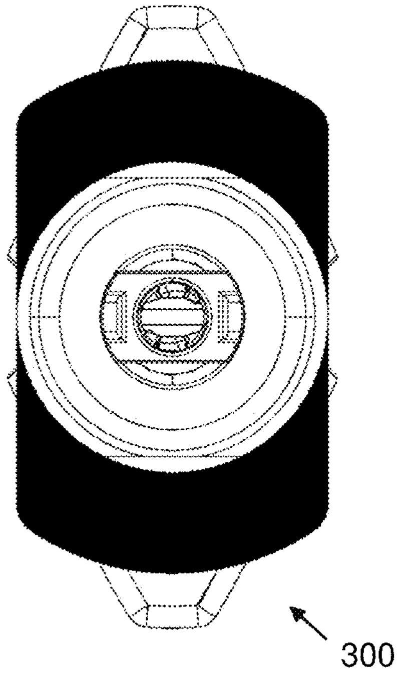
Figure 4G:
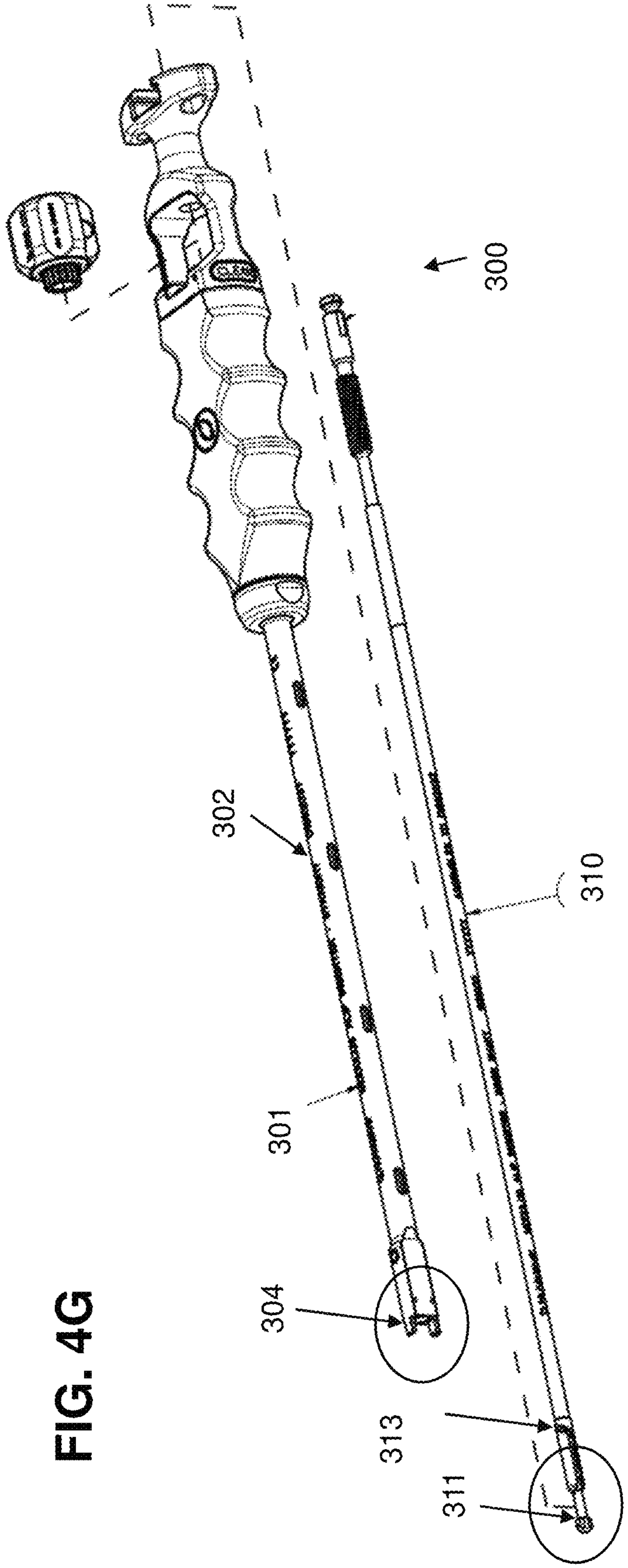
FIG. 4G shows an exploded view of an inserter according to an embodiment of the invention, including the outer shaft, the inner shaft, and the thumb wheel in accordance with an embodiment of the invention.
Figure 4H:
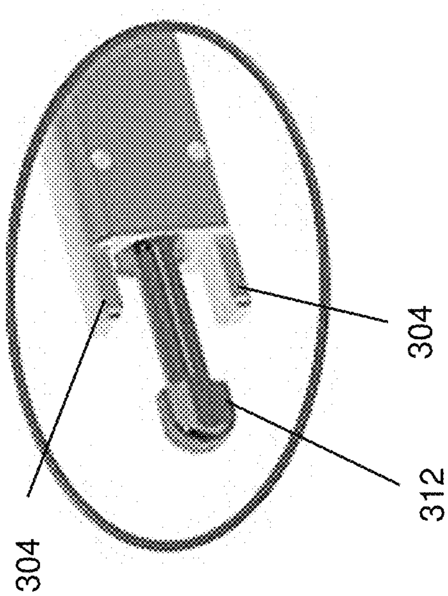
FIG. 4H shows an expanded view of the distal end of the inserter of FIG. 4G, in accordance with an embodiment of the invention.

In some embodiments, the outer shaft 301 may include two posts 304 at the distal end of elongate body 302. Posts 304 are best shown in FIGS. 4G-4H. Each of the two posts 304 may be configured to mate with a side engagement slot 113*b* (see, e.g., FIGS. 3C-3D) of the spinal implant 100, providing further engagement.

Bone Screws

With reference generally to FIGS. 5A-5D, bone screws 200 are disclosed herein, which are configured to be inserted into a spinal interbody or implant 100, and anchored into a vertebral bone. Bone screws 200 may include a screw head 202 with a keyed drive feature 203 configured to matingly engage with, or couple to a drive feature 403 of a driver such as removal driver 400, described further herein. For example, feature 203 may be shaped and dimensioned to provide a complementary fit with drive feature 403 of removal driver 400. In some embodiments, bone screw head 202 may include a cavity 201, and feature 203 may extend distally into cavity 201 from an inner surface of the bone screw head 202 surrounding the cavity 201.

Figure 7A:
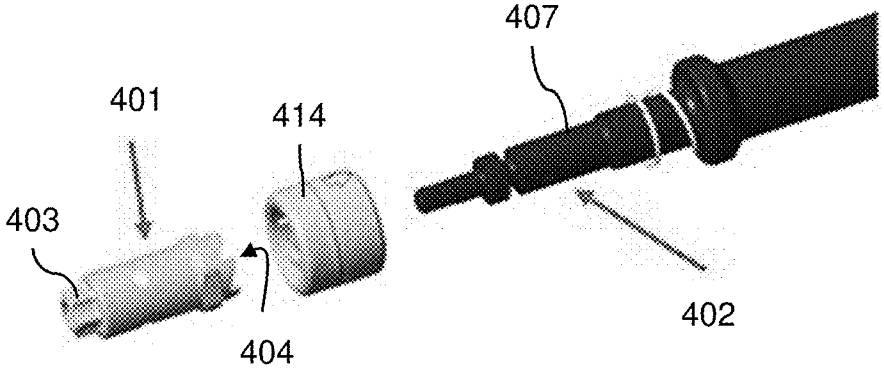
FIGS. 7A and 7B show perspective views of the distal portion of the outer sleeve and inner shaft of a removal driver in accordance with an embodiment of the invention.
Figure 7B:
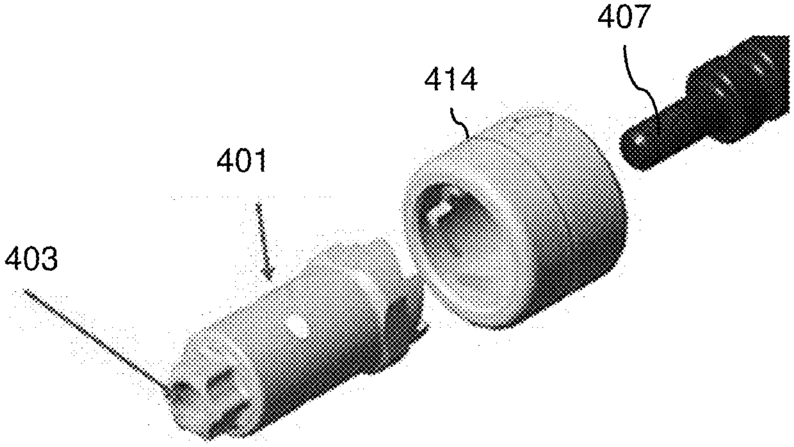

In some embodiments, feature 203 may include a trilobe shape 205 (FIG. 5D), having three lobes extending inwardly into the cavity 201 of the bone screw head 202. The trilobe 205 embodiment of feature 203 may allow for a thicker trilobe 405 (e.g., along the longitudinal axis of the screw) on the drive feature 403 of the removal driver 400 (see, e.g., FIG. 7B), thereby increasing strength of the driver. In some embodiments, the trilobe 205 on the bone screw 200 may be identical to a standard size hexalobe drive with 3 lobes removed, as can be seen in FIG. 5D. This may allow compatibility of screw 200 with standard hexalobe removal drivers of the same size. In some embodiments, feature 203 may further include an undercut 206 disposed distal to each lobe of the trilobe 205, as shown in FIG. 5A. The removal driver 400 can utilize a geometry that has a step 406 that catches this undercut 206 when rotated, as shown in, e.g., FIGS. 9B and 9D.

In various embodiments, screw 200 may have a length of, e.g., 15 mm, 17.5 mm, 20 mm, 22.5 mm, 25 mm, 27.5 mm, or 30 mm Head 202 of screw 200 may have a diameter of, e.g., 5.0 mm or 6.0 mm in certain embodiments.

Removal Drivers

As described above, disclosed herein are removal drivers 400 configured for removing bone screws 200 seated in a spinal interbody or spinal implant 100. FIGS. 6A-6B, 7A-7B, 8, 9A-9E, and 10A-10C show exemplary embodiments of the removal drivers 400 as disclosed herein.

In some embodiments, removal driver 400 includes an outer shaft 401 including a cavity, lumen, or cannulation 404 therewithin. The outer sleeve or shaft 401 may include a cannulated engagement feature 403 at its distal end. For example, in the embodiment shown in FIGS. 7A-7B, cannulated engagement feature 403 is a hexalobe-shaped drive feature, although other configurations are possible including, e.g., star drive, hex drive, or other driver geometries as would be understood by a person of skill in the art. Engagement feature 403 is configured to engage a corresponding feature 203 on bone screw head 202 (FIG. 8), as described above.

Cannulation 404, which extends axially through engagement feature 403 and outer shaft 401, is configured to allow a distal end of an inner shaft 402 to pass through the cannulation 404. The inner shaft 402 may comprise an elongated body 407, and a threaded distal end 410. Threaded distal end 410 may be configured to engage with internal threading 204 at or near the head 202 of a bone screw 200, thereby allowing unthreading of bone screw 200 from spinal implant 100.

In some embodiments, a clutch 414 marries the outer shaft 401 with the drive feature 403, which may be, e.g., a hexalobe shaped driver. Turning clockwise or counter clockwise, clutch 414 may be disengaged, and the inner thread of the inner shaft 402 may be configured to pull the removal driver 400 onto the screw head 202. This action is configured to push the deflectable latch 108 of implant 100 (FIG. 2D, among others) out of the way. Turning in the opposite direction, clutch 414 may be configured to engage and unthread bone screw 200 from implant 100. The bone screw thread 204 is retained to the driver 400 during removal.

Figure 8:
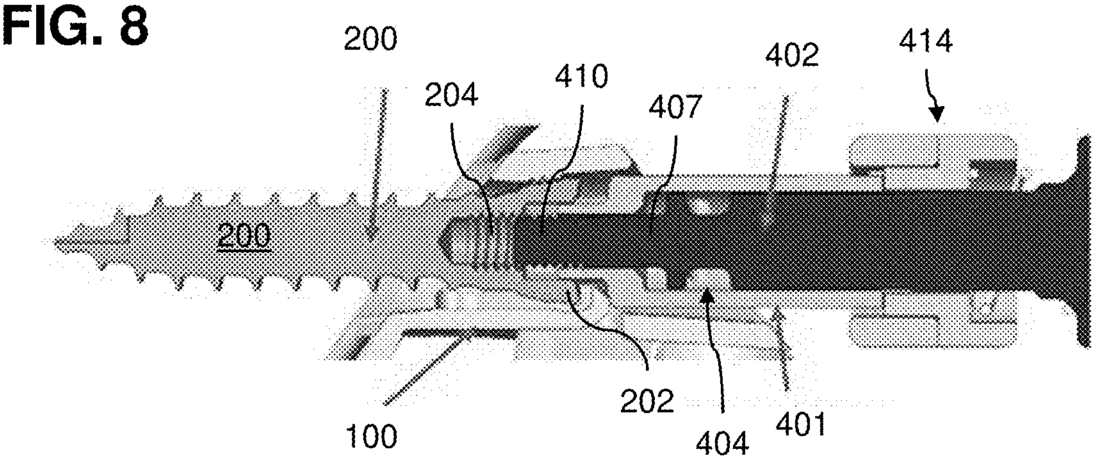
FIG. 8 shows a cross sectional view of a removal driver interacting with a bone screw in accordance with an embodiment of the invention.

FIG. 8 shows an exemplary embodiment of the removal driver 400 in engagement with a bone screw 200. Inner shaft 402 may be configured to translate at least in a distal direction relative to outer sleeve 401, through cannulation 404 of outer sleeve 401. This distal translation of inner shaft 402 relative to outer shaft 401 may be manually initiated by a user, e.g., a surgeon, in part by actuating clutch 414. In this position, outer sleeve 401 may be configured to deflect a deflectable latch 108 of spinal implant 100 latching on the thread head 202 of bone screw 200.

In some embodiments, when inner shaft 402 is securely coupled to the threading 204 on the bone screw head 200, the outer shaft 401 may translate distally relative to the inner shaft 402. In some particular embodiments, the outer sleeve 401 can translate down onto the bone screw head 200 relative to the inner shaft 402, which is coupled to the bone screw head 202 to push the latch 108 (FIGS. 9B, 9D) out of the way. At this point, screw 200 can be unthreaded and removed from the implant 100.

In some embodiments, the cannulated drive feature 403 may be hexalobe-shaped. Cannulated drive feature 403 may be disposed at or near a distal end of the outer sleeve 401.

Figure 6A:
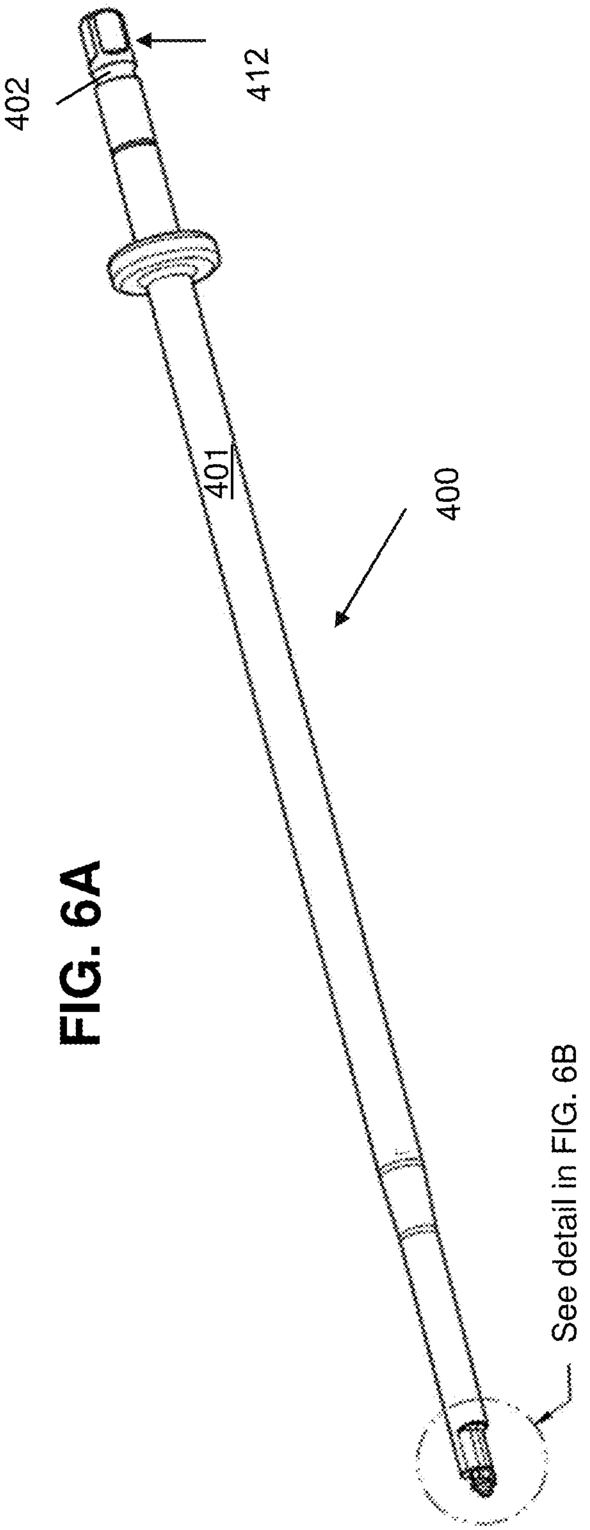
FIG. 6A shows a perspective view of a removal driver in accordance with an embodiment of the invention.
Figure 6B:
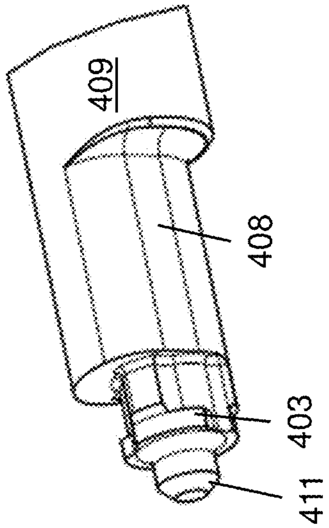
FIG. 6B shows a perspective view of the distal end of the removal driver of FIG. 6A in accordance with an embodiment of the invention.

In some embodiments, the threaded distal end 410 of the inner shaft 402 is positioned distally relative to a distal end of the outer sleeve 401. In other words, in such embodiments, threaded distal end 410 of inner shaft 402 extends distally through and out of outer sleeve 401 and cannulated drive feature 403. In some embodiments, drive feature 403 is configured to couple to feature 203 of the threaded head 202 of the bone screw 200 to facilitate engagement with the bone screw 200. In some embodiments, the removal driver 400 is configured to unlock the bone screw 200 when a longitudinal axis of the bone screw 200 is aligned with a longitudinal axis of the driver 400, as shown in FIG. 8. In some embodiments, the removal driver 400 is configured to unlock the bone screw 200 even when a longitudinal axis of the bone screw 200 is tilted or angled away from a longitudinal axis of the driver 400. In some embodiments, the inner shaft 402 further comprises a knob 412, disposed at a proximal end of inner shaft 402 (FIG. 6A). Knob 412 may be rotatable by a user thereby, causing rotation of the inner shaft 402.

Figure 10A:
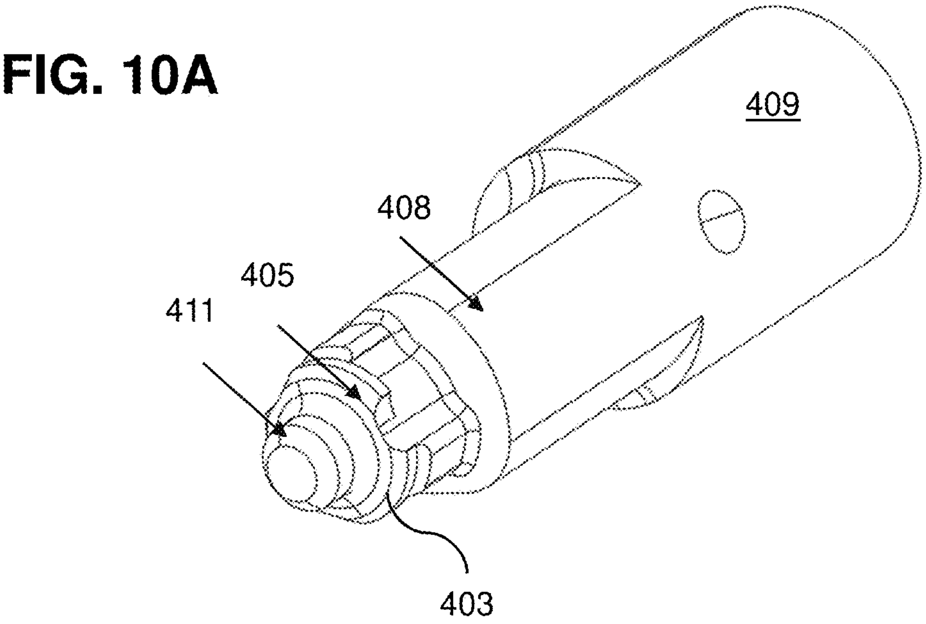
FIGS. 10A-10C show perspective views of a distal portion of a removal driver in accordance with an embodiment of the invention.
Figure 10B:
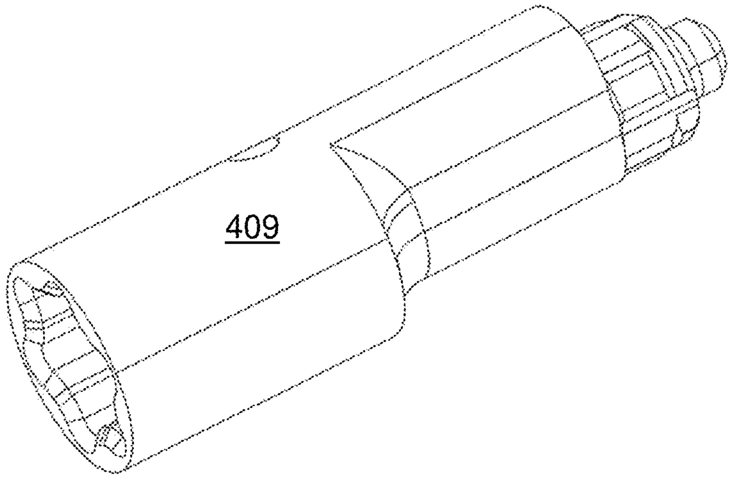
Figure 10C:
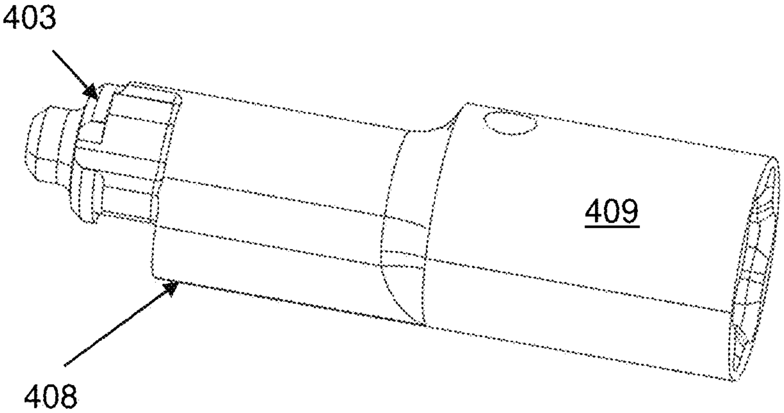

With reference to FIGS. 10A-10C, in some embodiments, removal driver 400 for removing a bone screw 200 from a spinal implant 100 may include a distal portion 409 having a distal end 411 and a drive feature 403 disposed proximally relative to distal end 411. Drive feature 403 may be configured to couple to a corresponding feature 203 of a head 202 of the bone screw 200 to facilitate engagement with the bone screw 200, in a manner previously described. In some embodiments, the distal end 411 is narrower than the drive feature 403 along a lateral direction or along a radial direction. In some embodiments, the drive feature 403 comprises a trilobe 405 (FIG. 10A) with three lobes, each lobe substantially equally separated from each other lobe. In some embodiments, the trilobe 205 on bone screw 200 is identical to a standard hexalobe size, with every other lobe removed (3 lobes in total), as can be seen in FIG. 10A. In some embodiments, the lobes of trilobe 405, 205 are equally spaced from one another along the circumference and each lobe has an identical size and shape. In some embodiments, the trilobe 405 of the removal driver 400 is sized and shaped so that the lobes can be inserted in the gaps between the adjacent lobes of the trilobe 205 of the bone screw head 202. In some embodiments, the trilobe 405 of the removal driver 400 are sized and shaped equally as the trilobe 205 of the bone screw head 200. In some embodiments, the trilobe 405 is configured to rotate and couple to an undercut 206 of the corresponding feature 205 of the head 202 of the bone screw 200.

The distal portion 409 of removal driver 400, in some embodiments, further includes a cam surface 408 disposed proximally relative to the drive feature 403, 405. The cam surface 408, when rotated, may be configured to outwardly deflect a deflectable latch 108 on an implant 100 from its position latching on the head 202 of the bone screw 200, thereby moving the deflectable latch out of a way of the bone screw.

Figure 9A:
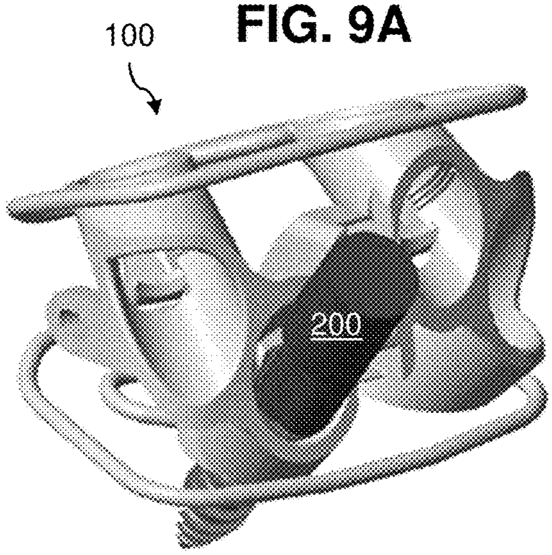
FIG. 9A shows a perspective view of the removal of a bone screw from the locked position in a spinal implant, using a removal driver in accordance with an embodiment of the invention.
Figure 9B:
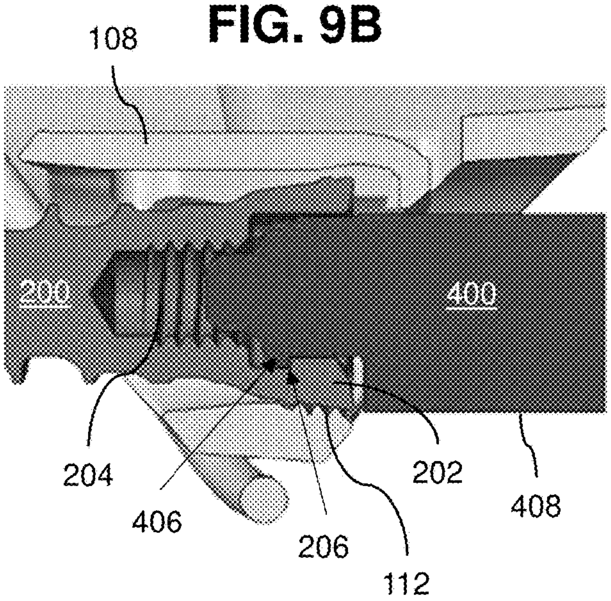
FIG. 9B shows a side cross sectional view of the removal of a bone screw from the locked position in a spinal implant, using a removal driver in accordance with an embodiment of the invention.
Figure 9C:
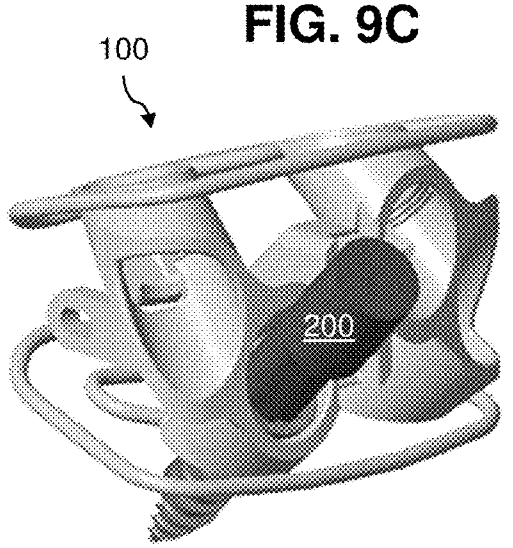
FIG. 9C shows a perspective view of the removal of a bone screw from the locked position in a spinal implant, using a removal driver in accordance with an embodiment of the invention.
Figure 9D:
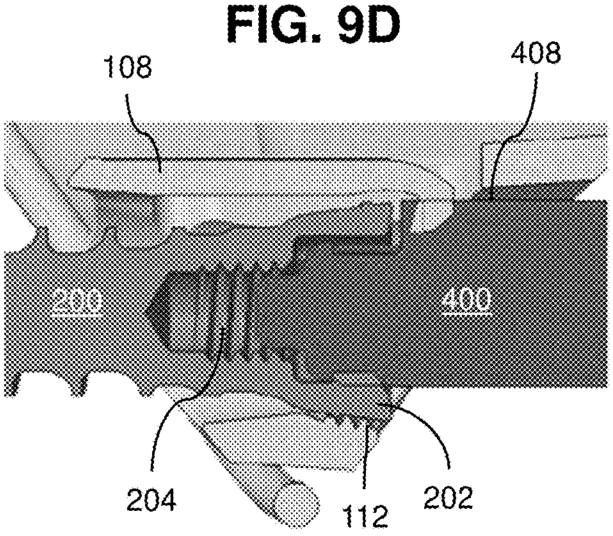
FIG. 9D shows a side cross sectional view of the removal of a bone screw from the locked position in a spinal implant, using a removal driver in accordance with an embodiment of the invention.
Figure 9E:
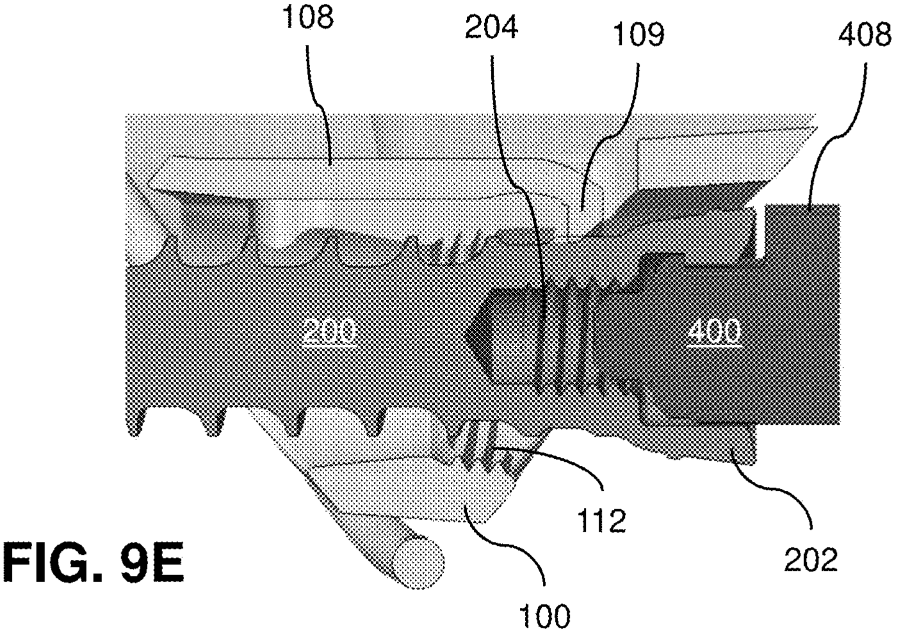
FIG. 9E shows a side cross sectional view of the removal of a bone screw from the locked position in a spinal implant, using a removal driver in accordance with an embodiment of the invention.

FIGS. 9A-9E shows an exemplary embodiment of the sequential operations during removal of the bone screw 200 using the bone screw removal driver 400 as disclosed herein. FIGS. 9A and 9B show the spinal implant 100 simplified form, with only a frame structure and a fully seated bone screw 200 latched by the deflectable latch 108. In this particular embodiment, the removal driver 400 is inserted on the head 202 of bone screw 200. The removal driver 400 is inserted and then rotated so that the trilobe drive feature 405 (FIG. 10A) couples to the undercut 206 of the head 202 of bone screw 200, distal to the trilobe feature 205 of the head 202 of bone screw 200. Subsequently, in FIGS. 9C-9D, rotation of the removal driver 400 along with the bone screw 200 rotates the cam surface 408 of the removal driver 400. Such rotational movement of the cam surface 408 (e.g., without translation) pushes the deflectable latch 108 and its lip 109 out of the way of the bone screw 200, so that sequential unthreading of the bone screw 200 can be performed. This process enables removal of the bone screw 200 from the spinal implant 100. FIG. 9E shows that the bone screw 200 is unthreaded and ready to be pulled away from the spinal implant 100.

In some embodiments, removal driver 400 advantageously allows for a single piece (e.g., solid) driver distal portion that can positively retain bone screw 200 during its removal. In some embodiments, the removal driver 400 can be used to unlock locking mechanisms that feature springs, tabs, or flexible features that cover the bone screws 200 in various spinal applications including but not limited to cervical plates, interfixated cages, and Anterior Lumbar Interbody Fusion (ALIF) plates. The removal driver 400 disclosed herein can also be used with a conventional u-joint in an angled application, as would be understood by a person of skill in the art.

Screw Drivers

With reference to FIGS. 11A-11D and 12A-12C, disclosed herein are screw drivers 500 for inserting a bone screw 200 into a spinal implant 100.

In some embodiments, screw driver 500 features a flexible tab component 501 that is permanently assembled to the elongate body 506 of driver 500. The flexible tab 501 can elastically deflect outwardly when a screw 200 is loaded on to the tip which creates an interference fit with the bone screw 200. This interference fit retains the screw 200 during use. In some embodiments, the flexible tab 501 advantageously removes minimal material from the driver distal portion which aids in strength of the screw driver 500.

In some embodiments, the screw driver 500 includes an elongate body 506 having a distal portion 507, a distal end 504, and a drive feature 505 located on an outer surface 508 of the driver 500 proximal to the distal end 504. The drive feature 505 may be configured to engage a corresponding feature 205 of a head 202 of the bone screw 200 to facilitate engagement with bone screw 200. As shown in FIGS. 11A-11D and FIGS. 12A-12C, in some embodiments, drive feature 505 includes a trilobe shape, having three lobes **505*a* separated by three grooves 505*b*. Lobes 505*a* and grooves 505*b* may be evenly distributed around the circumference of the cross section of driver 500. Each of the three grooves 505*b* may be positioned between two adjacent lobes 505*a*** of the trilobe.

Figure 11A:
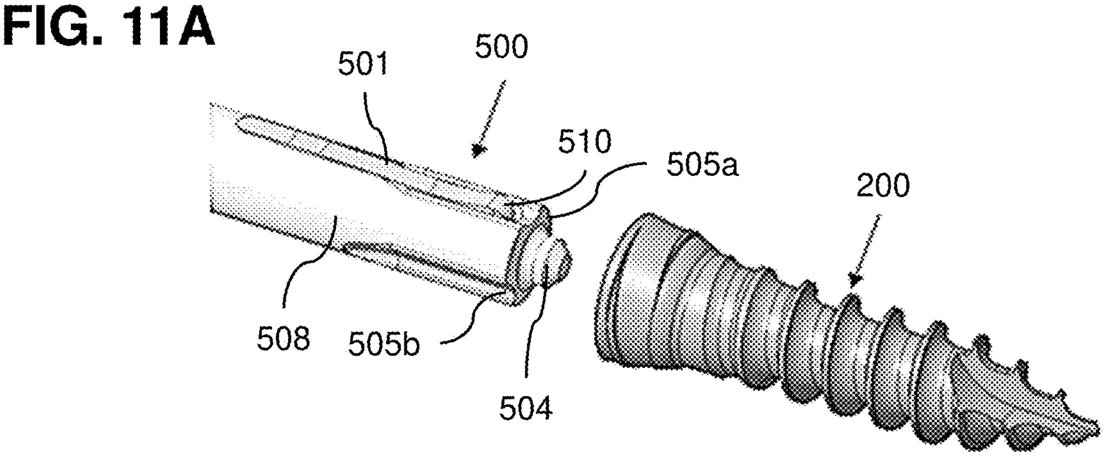
FIGS. 11A-11D show a perspective view, a side cross sectional view, a side view, and a cross sectional view, respectively, of a screw driver and its engagement with a bone screw in accordance with an embodiment of the invention.
Figure 11B:
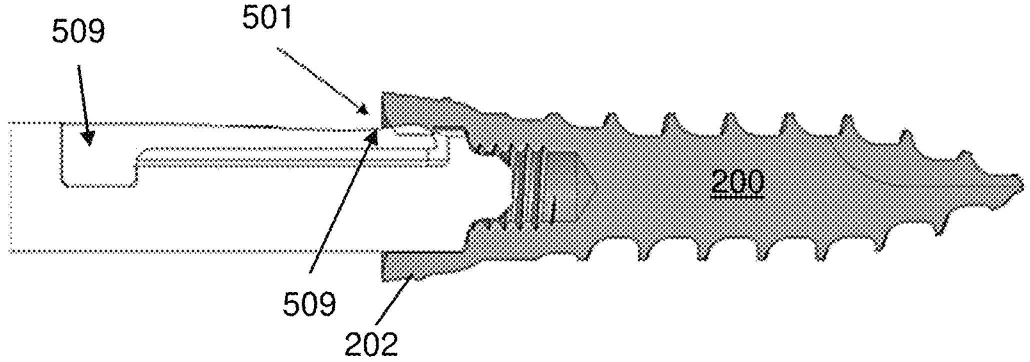
Figure 11C:
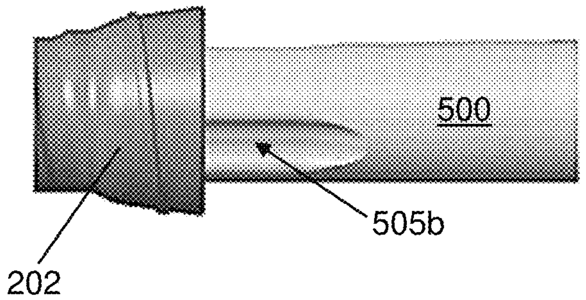
Figure 11D:
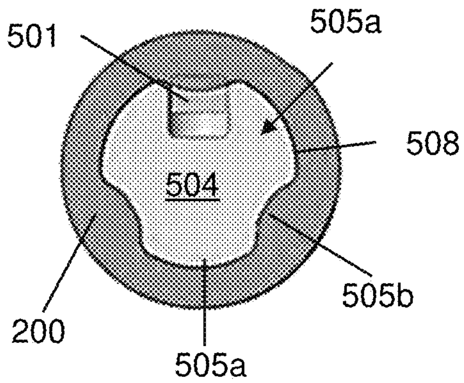
Figure 12A:
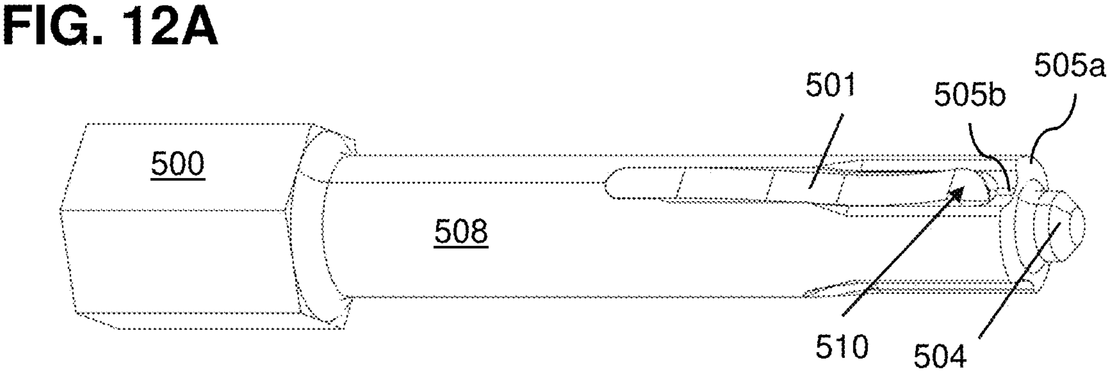
FIGS. 12A-12C show perspective and side views of the screw driver of FIGS. 11A and 11B, in accordance with an embodiment herein.
Figure 12B:
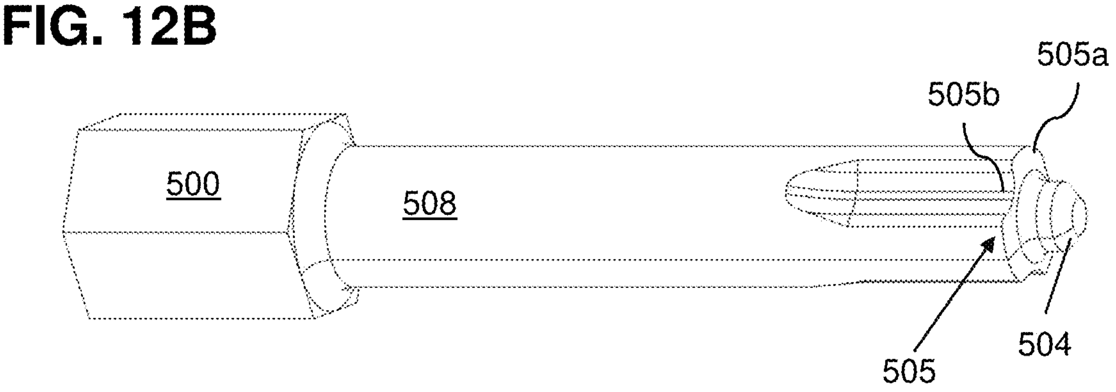
Figure 12C:
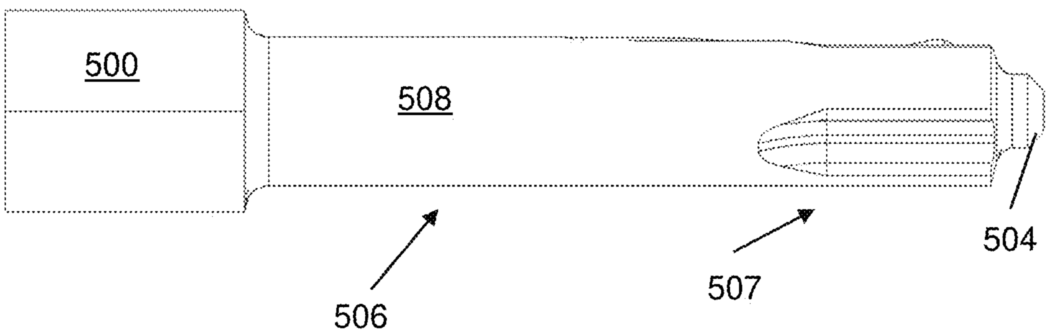

Screw driver 500 may further include a flexible tab 501 extending toward the distal end 504. Flexible tab 501 may include a proximal portion 509 that is fixedly anchored to elongate body 506. The proximal portion 509 of tab 501 may be thicker than a distal portion thereof, for example, in a radial direction. Flexible tab 501 also may include a distal portion 510 that is bendable or movable radially inward or outward. The movement of the distal portion 510 can be caused by a biasing energy or force. In some embodiments, flexible tab 501 is configured to bend or move inward from its resting position when the bone screw 200 is being loaded onto the screw driver 500. In some embodiments, flexible tab 501 sits radially outward relative to outer surface 508 of distal portion 504 of screw driver 500, at its resting state or balanced state, as can be seen in FIGS. 11A, 12A, and 12C. After bone screw 200 is properly loaded onto the screw driver 500, flexible tab 501 may be configured to bias radially outwardly to retain the bone screw 200 on the driver 500. In some embodiments, flexible tab 501 may sit lower than, i.e. radially inward relative to, or flush with outer surface 508 of distal portion 504 of screw driver 500, as can be seen in FIG. 11D. FIG. 11D shows a cross-sectional view of distal portion 504 of bone screw driver 500 with a bone screw 200 loaded thereon. In some embodiments, the flexible tab 501 comprises metal, alloy, or any other flexible material. In some embodiments, the flexible tab 501 is positioned at least partly within a groove 505*b* on the outer surface 508 of the driver 500, as shown in FIGS. 11A, 11D, and 12A.

In certain embodiments, the distal end 504 may be narrower, e.g., radially, than the drive feature 505, and/or the circumference of the distal end 504 may be smaller than the circumference of the rest of the distal portion 504 of the screw driver 500.

Instruments for Spinal Fusion Implant

As described above, an inserter 300 is provided for use in the insertion of implant 100, according to embodiments of the invention. With reference generally to FIGS. 13-15, 16A-16F, 17A-17C, 18A-18B, 19, and 20, a number of particular inserter configurations and embodiments are further described herein.

Straight Inserter

Figure 13:
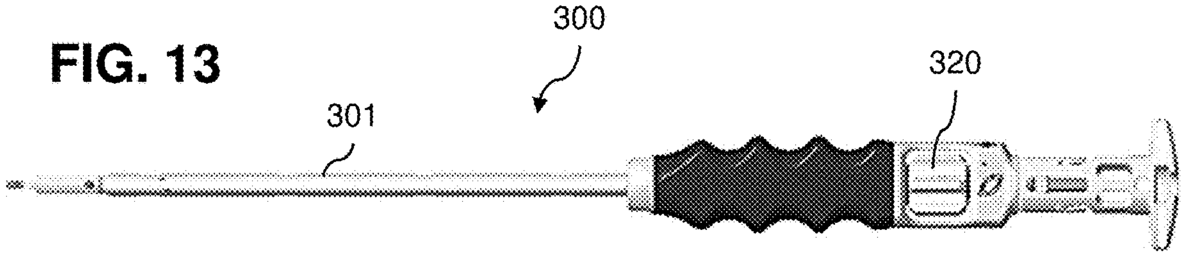
FIG. 13 shows a side view of an inserter according to an embodiment of the invention.
Figure 14:
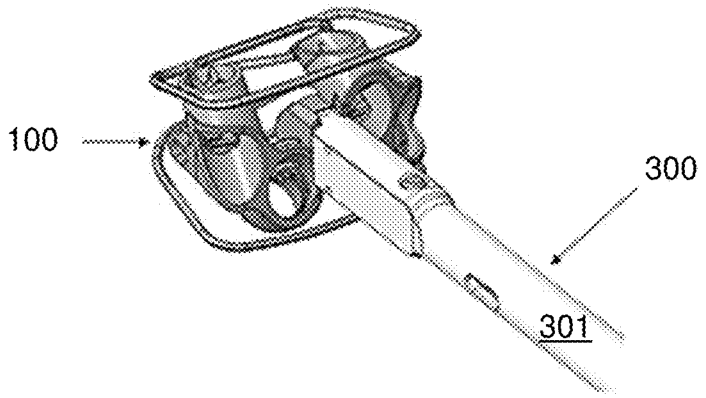
FIG. 14 shows a perspective view of an implant engaged with a straight inserter in accordance with an embodiment of the invention.
Figure 15:
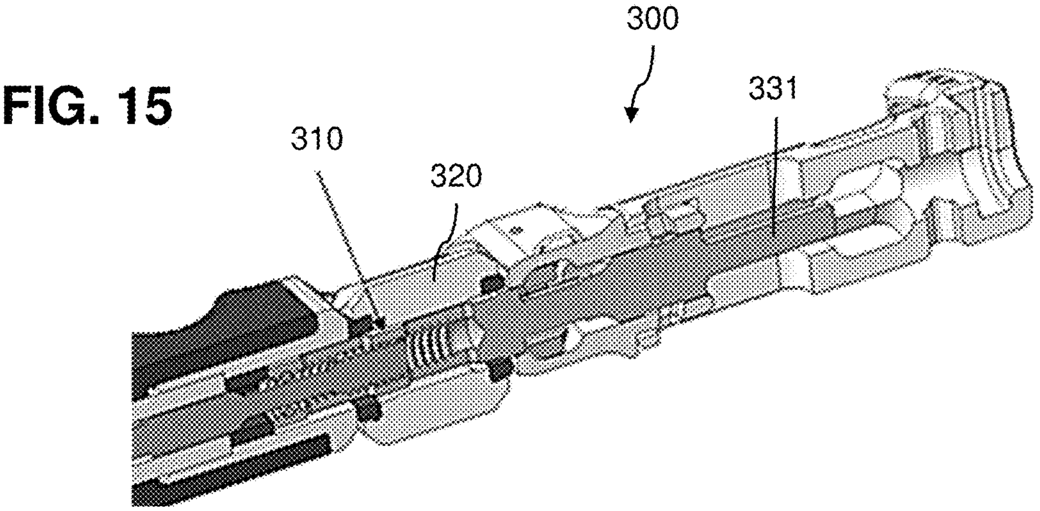
FIG. 15 shows a cross sectional view of an inserter in accordance with an embodiment of the invention.

Turning first to FIGS. 13-15, an inserter 300 is illustrated in a straight configuration, according to an embodiment of the invention. As described previously, the inserter 300 may include an outer shaft 301 having an elongate body 302 with a cavity or lumen disposed therein. Inner shaft 310 may be disposed within the lumen of elongate body 302. Inner shaft 310 may include a distal tip 311 including an engagement feature 312 configured to matingly engage an engagement aperture 113*a* on implant 100 in use as described above. A pair of opposing posts 304 may be provided on a distal tip of outer shaft 302. Posts 304 may be configured to engage a corresponding pair of engagement slots 113*b* on implant 100 in use.

Figure 16A:
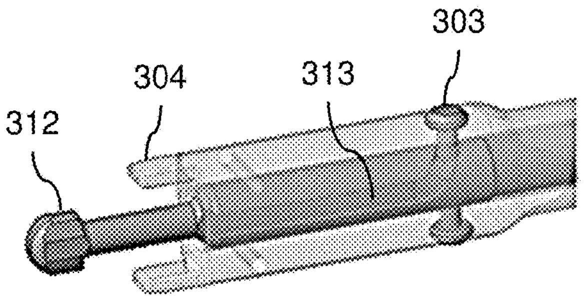
FIGS. 16A and 16B illustrate perspective views of a distal tip of an inserter in an unlocked and locked position, respectively, relative to a spinal implant, according to an embodiment of the invention.
Figure 16B:
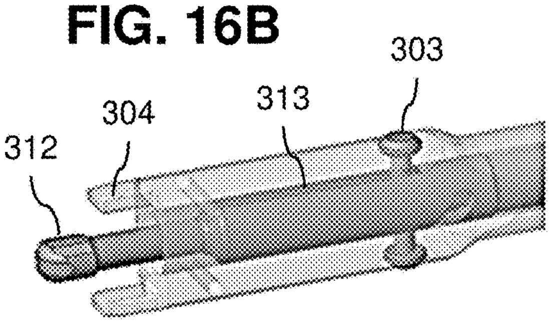

A barrel cam element 313 may be provided at a distal end of inner shaft 310, disposed proximally relative to distal tip 311 and engagement feature 312. Barrel cam element 313 is configured to provide a non-threaded connection to implant 100. A pair of opposing pins 303, configured to engage with barrel cam element 313, may extend radially inwardly from an inner surface of elongate body 302. The two opposing pins 303 may be disposed at or near a distal end of a barrel cam element 313 when inserter 300 is in an unlocked position (FIG. 16A). The two opposing pins 303 are configured to rotate, e.g., approximately 90° about a circumference of inner shaft 310, and translate distally as inserter 300 moves into a locked position (FIG. 16B). Barrel cam element 313 is illustrated in its unlocked configuration, i.e., unlocked from implant 100, in FIG. 16A, and in its locked configuration, i.e., locked to implant 100, in FIG. 16B.

A thumbwheel 320 (FIG. 13) may be threadedly coupled to a proximal end of the inner shaft 310. Thumbwheel 320 may be configured to be rotated by a user and to cause rotation of barrel cam element 313, thereby causing simultaneous rotation and translation of the inner shaft 310 relative to the outer shaft 302 and the spinal implant 100. This also causes the rotation and translation of engagement feature 312, depicted in the transition from FIG. 16C to 16D, and 16E to 16F. In some embodiments, rotation of the thumb wheel 320 may cause simultaneous rotation and translation of the inner shaft 310 relative to the outer shaft 302 and may cause coupling or uncoupling of the distal tip 311 and engagement feature 312 of the inner shaft 310 with the engagement aperture 113*a* of the implant 100, thereby locking or unlocking the inserter 300 to or from the spinal implant 100.

Figure 16C:
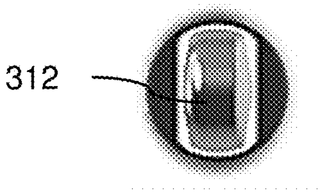
FIGS. 16C and 16D illustrate distal end view of an inserter in an unlocked and locked position, respectively, relative to a spinal implant, according to an embodiment of the invention.
Figure 16D:
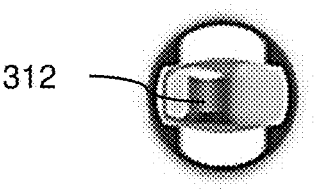
Figure 16E:
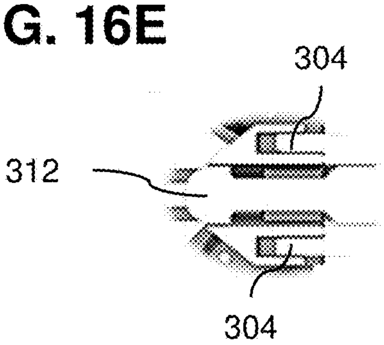
FIGS. 16E and 16F illustrate cross sectional views of an inserter in an unlocked and locked position, respectively, relative to a spinal implant, according to an embodiment of the invention.
Figure 16F:
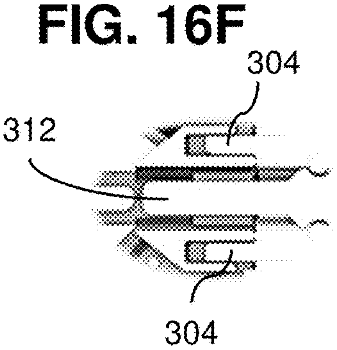

The resulting positions of engagement feature 312 and posts 304, based on the position of posts 303 in barrel cam element 313, are illustrated in FIGS. 16C-16F. Engagement feature 312 is shown in FIGS. 16C and 16E in its unlocked configuration, i.e., unlocked from implant 100, and in its locked configuration, i.e., locked to implant 100, in FIGS. 16D and 16F. Barrel cam element 313 is configured to allow the inserter 100 to lag (or pull back) the implant 100 in a manner similar to a threaded engagement, and provides a rigid connection to the implant 100. At the same time, barrel cam element 313 avoids some of the sticking/galling issues often seen with threaded attachments to titanium devices.

Figure 17A:
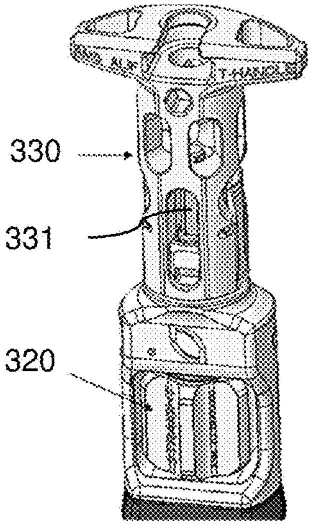
FIGS. 17A-C show perspective views of aspects of a detachable T-handle in accordance with embodiments of the invention.
Figure 17B:
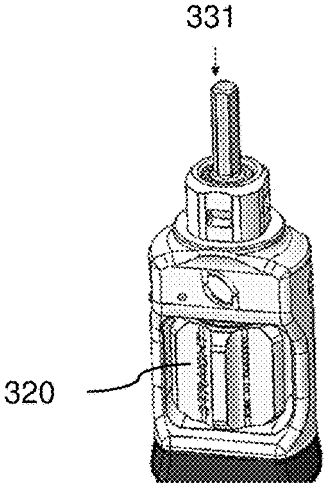
Figure 17C:
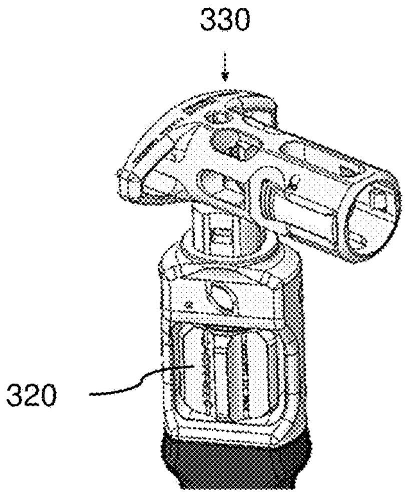

In certain embodiments, as shown in FIG. 15, inner shaft 310 may comprise a multi-piece shaft, and may be coupled in a manner configured to allow inserter 300 to be actuated, i.e., engaged and disengaged from implant 100, via thumbwheel 320 or a detachable t-handle wrench 330. The detachable t-handle wrench can be removed from its position on the inserter 300 as shown in FIG. 17A, and applied to the proximal shaft hex connection 331 as shown in FIG. 17B, in order to provide additional torque in use in the configuration as shown in FIG. 17C.

Angled Inserters

Turning next to FIGS. 18A-18B, 19, and 20, another embodiment of an inserter 300 is illustrated, in an angled configuration. The angled inserter 300 of FIGS. 18A-18B, 19, and 20 includes components similar to those described above relative to the straight inserter 300 of, e.g., FIGS. 13-14. Like the straight inserter, the angled inserter includes a barrel cam element 313 configured to provide a non-threaded connection between inserter 300 and implant 100.

Figure 18A:
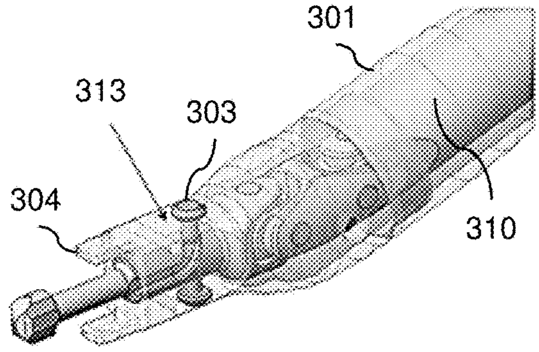
FIGS. 18A-B illustrate perspective views of aspects of an inserter in accordance with embodiments of the invention.
Figure 18B:
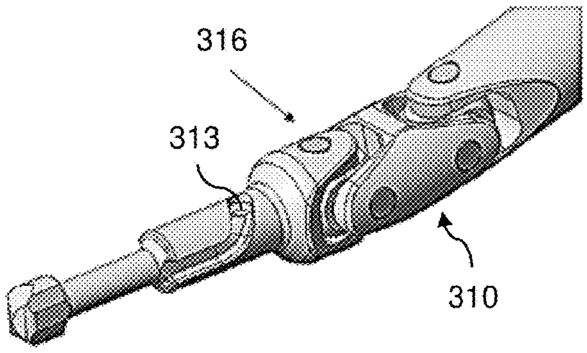
Figure 19:
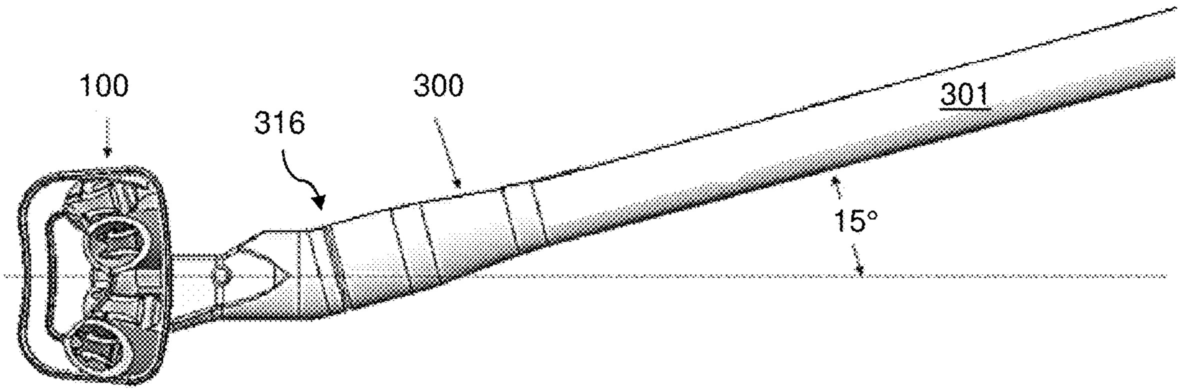
FIG. 19 illustrates a side view of a lateral angled inserter engaged with a spinal implant according to an embodiment of the invention.
Figure 20:
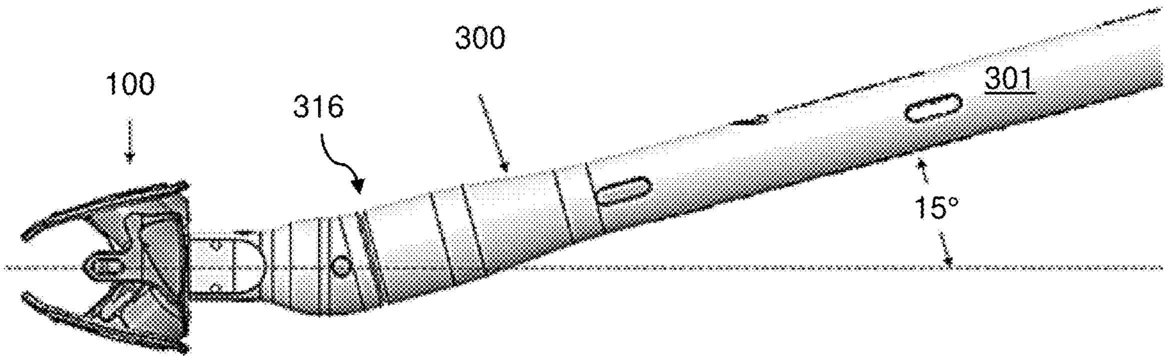
FIG. 20 illustrates a side view of a cranial-caudal angled inserter engaged with a spinal implant according to an embodiment of the invention.

In the embodiment of FIGS. 18A-18B, inserter 300 includes an outer shaft 301 having an elongate body 302 with a cavity or lumen disposed therein. Inner shaft 310 is disposed within the cavity. Inner shaft 310 includes a coupled universal joint 316 that is flexible. Joint 316 is configured to adjust the angle of the inserter 300 up to approximately 15° relative to a longitudinal axis of outer shaft 301 in one of a number of anatomical planes. In one embodiment, shown in FIG. 19, a lateral footed inserter is shown, featuring an angle of approximately 15° in a lateral direction relative to the longitudinal axis of outer shaft 301. In another embodiment, shown in FIG. 20, a cranial-caudal inserter is shown, featuring an angle of approximately 15° in a cranial-caudal direction relative to the longitudinal axis of outer shaft 301. The inserters of FIGS. 19 and 20 are configured for use in particular implant insertion procedures. For example, a lateral footed inserter as shown in FIG. 19 may be used in an anterior lumbar interbody fusion (ALIF) procedure using a lateral incision approach. The lateral footed inserter of FIG. 19 may be particularly useful in a supine ALIF procedure. Such a method may include positioning the patient in a supine position, creating a lateral incision, and inserting an implant such as, e.g., implant 100, through the incision into the space between target vertebrae, e.g., between lumbar vertebrae, using the lateral footed inserter as shown in, e.g., FIG. 19.

In another example, a cranial-caudal (C-C) inserter as shown in FIG. 20 may be used in an ALIF procedure, particularly in cases in which the patient exhibits a high sacral slope or other challenging anatomy is present. The C-C inserter of FIG. 20 may be particularly useful in an ALIF procedure that includes inserting an implant between the L5 and S1 vertebrae. Such a method may include positioning the patient in a lateral decubitus position, creating a lateral or oblique incision, and inserting an implant such as, e.g., implant 100, through the incision into the space between target vertebrae, e.g., the L5 and S1 vertebrae, using the angled inserter as shown in, e.g., FIG. 20.

In some embodiments, the head of inserter 300, i.e., the portion of inserter 300 that is distal of joint 316, is slim enough in profile to allow a driver such as, e.g., removal driver 400 or screw driver 500, to access and engage with a screw 200 that is being inserted into or removed from a fixation aperture 107 of implant 100 while inserter 300 is engaged with and coupled to implant 100 via engagement feature 312 and posts 304. This provides additional stability during the insertion and removal procedures.

Slap Mallet

Turning next to FIGS. 21-26, a slap mallet 600 is described herein. The slap mallet 600 is configured to provide a user with the ability to mallet and reverse mallet (slap hammer) in a single tool. Traditionally, surgeons use separate mallets and slap hammers to impact other instruments when placing or removing implants such as, e.g., implant 100. With multiple tools, additional passes between the surgeon and operating room tech are required. Slap mallet 600 is configured to provide a single device which the surgeon can manipulate independently, to provide three distinct modes of impact for insertion into and retraction from an incision. For example, a first mode of impact may be useful for insertion, in which force is transmitted through mallet head 607 and/or other smooth surfaces. In another mode, forces may be applied that are useful for removal through an incision. These forces may be applied through a U-shaped channel 608 in mallet head 607, which extends proximally from a distal end of mallet head 607. Channel 608 may be configured to enable a user to backmallet on an instrument to apply axial force in an outward direction relative to an incision. Removal force may alternatively be applied by a recessed flat surface feature 609 on mallet head 607. Recessed flat surface feature 609 may be configured to mate with a complementary sized and shaped feature on another instrument, e.g., an inserter. A third force may be applied using slap mallet 600 in an axial or inline direction.

In one embodiment, slap mallet 600 includes a first shaft 601 and a second shaft 602 that is disposed at least partially within first shaft 601. First shaft 601 may be configured for use as a handle, while second, inner shaft 602 may be configured to function as an extension rod. Slap mallet 600 may further include a button 603, a biasing element 604, a pin 605, and a clutch assembly 606. In one embodiment, slap mallet 600 includes a mallet head 607 may be coupled to first shaft 601, with second shaft 602 disposed at least partially within first shaft 601. First shaft 601 may be configured for use as a handle, while second shaft 602 may be configured for use as an extension rod.

Figure 21:
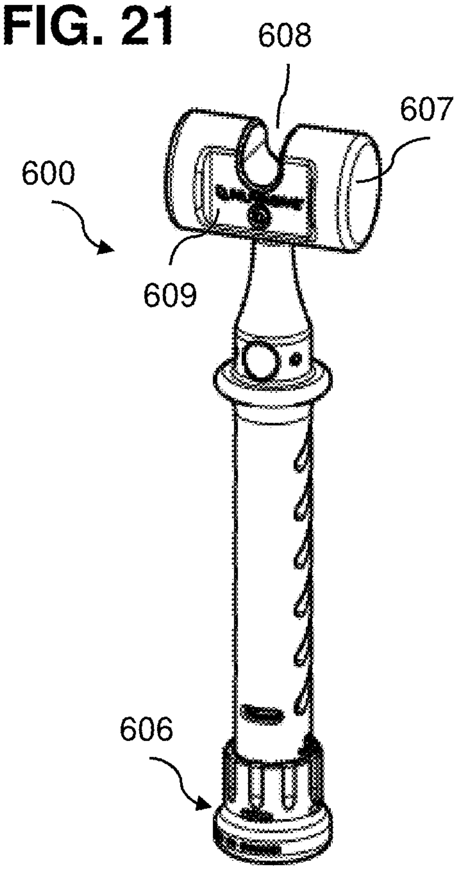
FIG. 21 shows a perspective view of a slap mallet in accordance with an embodiment of the invention.
Figure 22:
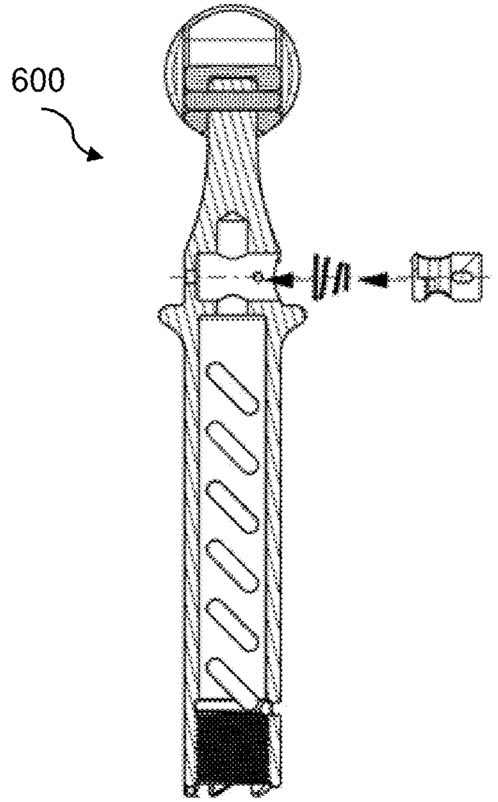
FIG. 22 illustrates a cross sectional view of a slap mallet in accordance with an embodiment of the invention.
Figure 23:
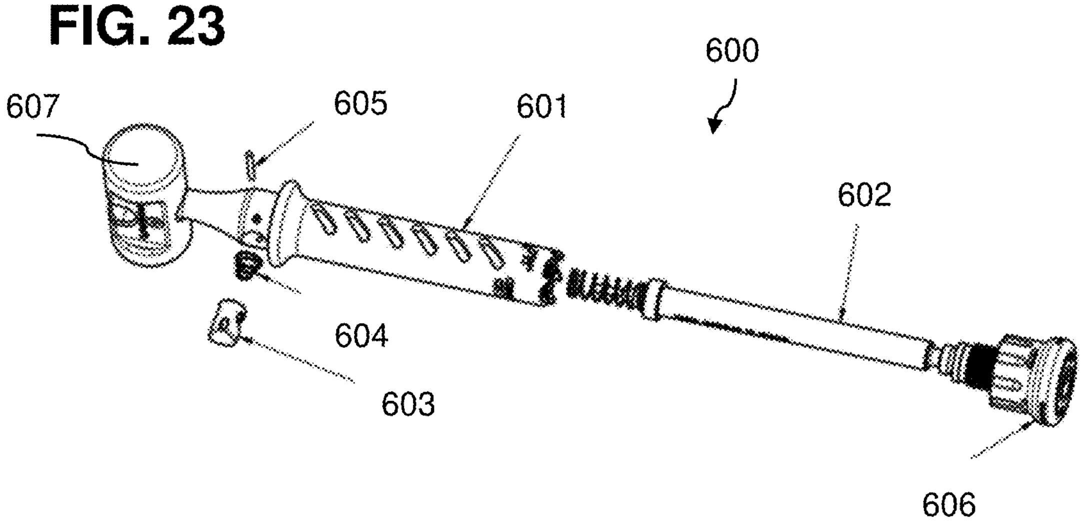
FIG. 23 illustrates an exploded perspective view of a slap mallet in accordance with an embodiment of the invention.
Figure 24:
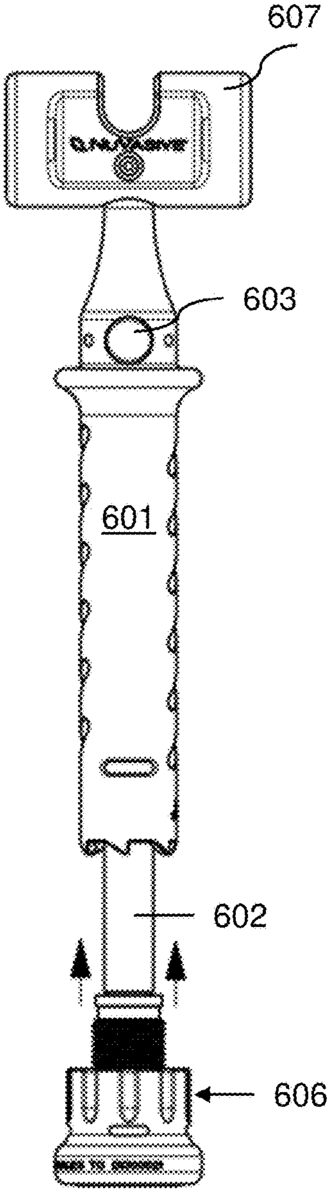
FIGS. 24-26 show side views of a slap mallet in accordance with an embodiment of the invention.
Figure 25:
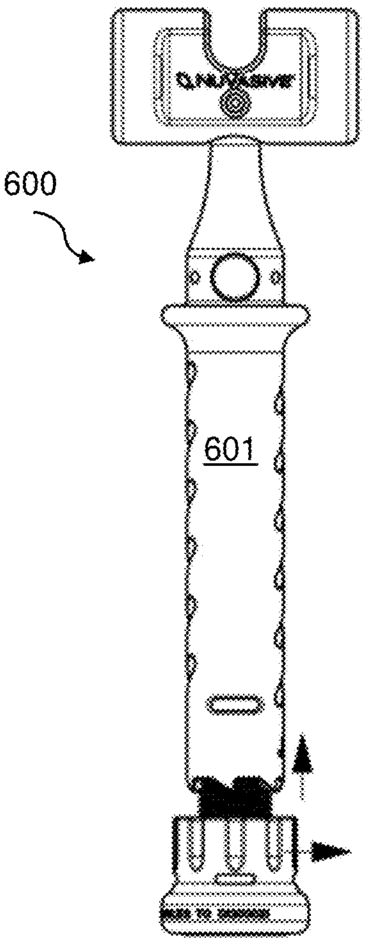

Slap mallet 600 may be used like a standard slap hammer with second rod 602 disposed substantially or entirely within first shaft 601, as shown in, e.g., FIG. 21. In this position, second shaft 602 may be retracted into first shaft 601 and maintained in that position by biasing element 604 when slap mallet 600 is being used as a mallet. Biasing element 604 may be, e.g., a spring, thread or other means for retaining the position of second shaft 602.

Figure 26:
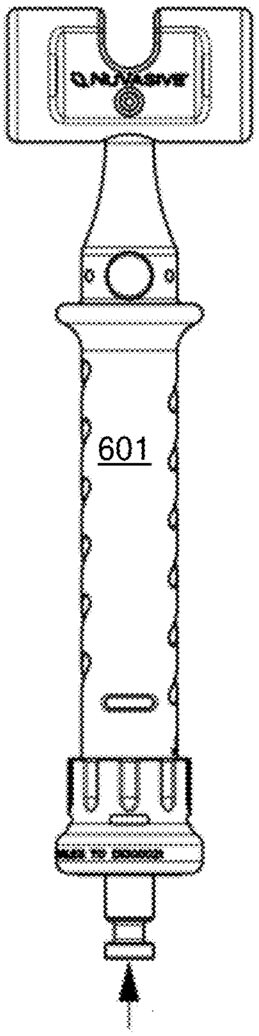

To use slap mallet 600 as a slaphammer, second shaft 602 may be extended proximally, and slap mallet 600 may be attached to an instrument in a manner readily understandable to one of skill in the art. A quick attachment can be implemented between second shaft 602 and an instrument for rapid engagement and disengagement with the instrument. Alternatively, the second shaft 602 can be threaded into the instrument. Keying the second shaft 602 to the first shaft 601 of the mallet allows for each rotation of the first shaft 601 to thread the second shaft 602 into the instrument. In certain embodiments, t-handle 330, shown in FIGS. 17A-17C with respect to inserter 300, may further be coupled to a proximal end of inner shaft 602 (FIG. 26). In use, t-handle 330 may enable a user to apply force in different ways, including in different directions.

Trial Inserters

Turning next to FIGS. 27-34, a trial inserter 700 is provided in accordance with embodiments of the invention. Trial inserter 700 may include a distal component 701 that is threaded and configured to couple directly to an implant such as implant 100 or trial.

Trial inserter 700 may include a shaft comprising multiple linked components, of which distal component 701 may be the terminal and distal-most. Distal component 701 may be considered a first link in the linked shaft, and may be coupled at a proximal end thereof to a second link 702. A rounded distal end of second link 702 is received within a proximal end of distal component 701, and is coupled in place by coupler 704, which passes through a distal aperture 703 in second link 702. Coupler 704 may be, e.g., a pin. Second link 702 may further include a rounded proximal end which is received within a distal end of barrel link 705, in a manner similar to a ball and socket joint, providing rotational flexibility between second link 702 and barrel link 705. When the proximal end of second link 702 is positioned within the distal end of barrel link 705, an aperture 706 is created that passes through the joint between the two components 702, 705. Aperture 703 may be rotated relative to aperture 706, for example by about 90°.

Returning to aperture 706, coupler 704 passes through aperture 706, thereby coupling the components together. Aperture 706 may have an hourglass shape, such that aperture 706 may have a smaller diameter in the center than at the open ends of the aperture, such that the axial center of coupler 704 is permitted less rotational movement than the ends thereof. This arrangement of coupler 704 within aperture 706 is configured to allow a range of motion of approximately 10° from the axis of coupler 704.

Barrel link 705 is configured to provide translation of the whole distal linkage, including distal component 701, second link 702, and barrel link 705, relative to shaft 707. Barrel link 705 connects to the main shaft 707 through a keyed drive feature 708 and coupler 704 allowing for translation and torque transmission. Keyed drive feature 708 may be, e.g., a square drive. Couplers 704 disposed at the proximal and distal ends of barrel link 705 may be substantially parallel to one another. A biasing element 709 such as, e.g., a coil spring, may be disposed between barrel link 705 and shaft 707. Biasing element 709 is configured to push the linkage 701, 702, 705 distally to aid in connection. Thus, the distal component link 701 is pinned to the second link 702, which is pinned to the barrel link 705, which is pinned to the main shaft 707, capturing the plunger spring 709 between the barrel link 705 and the shaft 707.

Figure 31:
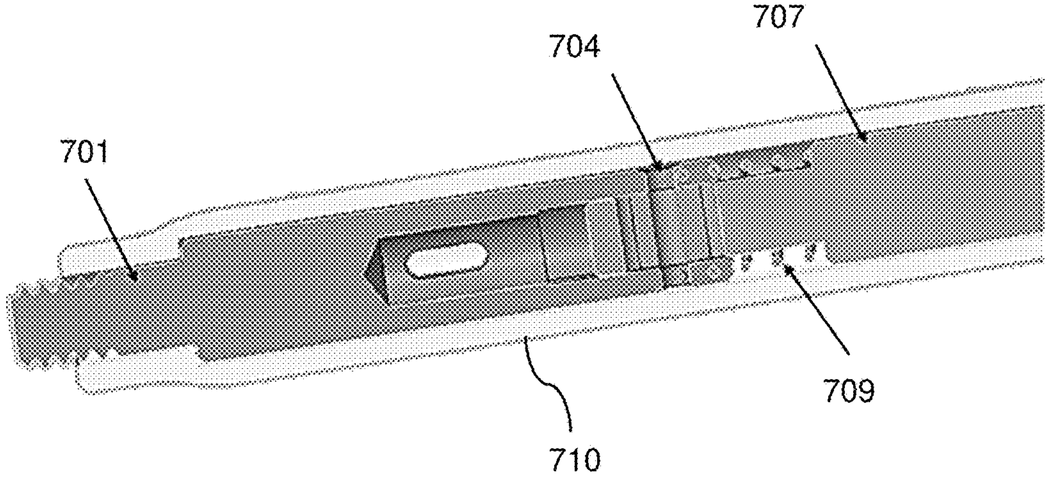
FIG. 31 shows a cross sectional view of a trial inserter in accordance with an embodiment of the invention.
Figure 32:
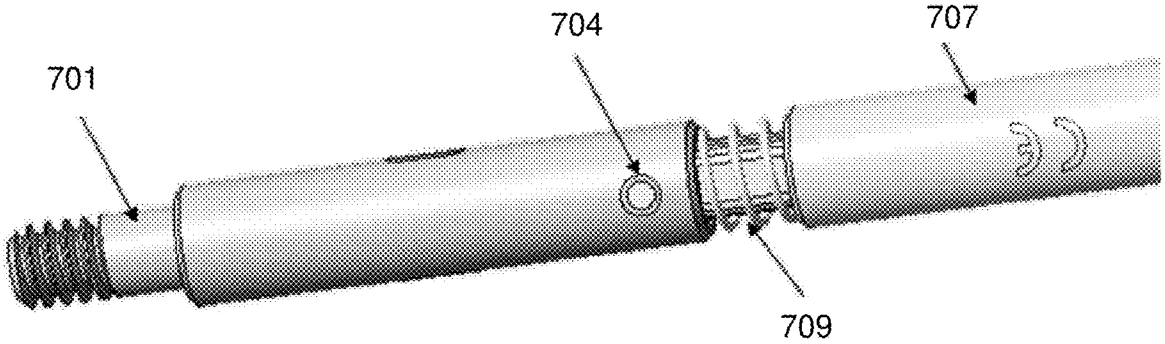
FIG. 32 shows a perspective view of a portion of a trial inserter in accordance with an embodiment of the invention.
Figure 33:
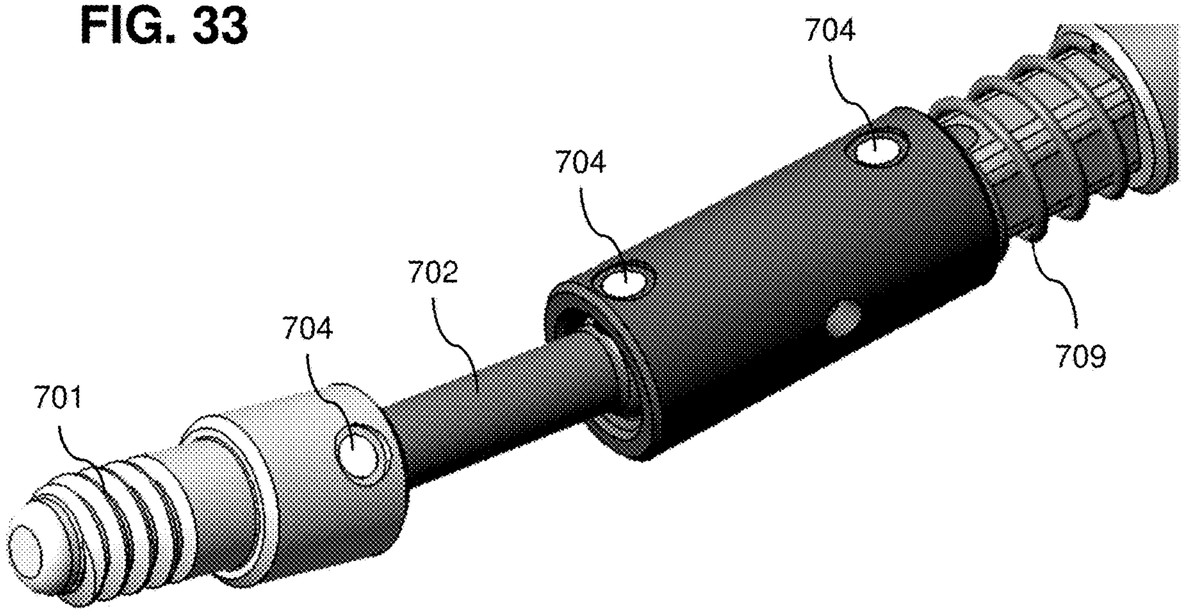
FIG. 33 shows a perspective view of a portion of a trial inserter in accordance with an embodiment of the invention.
Figure 34:
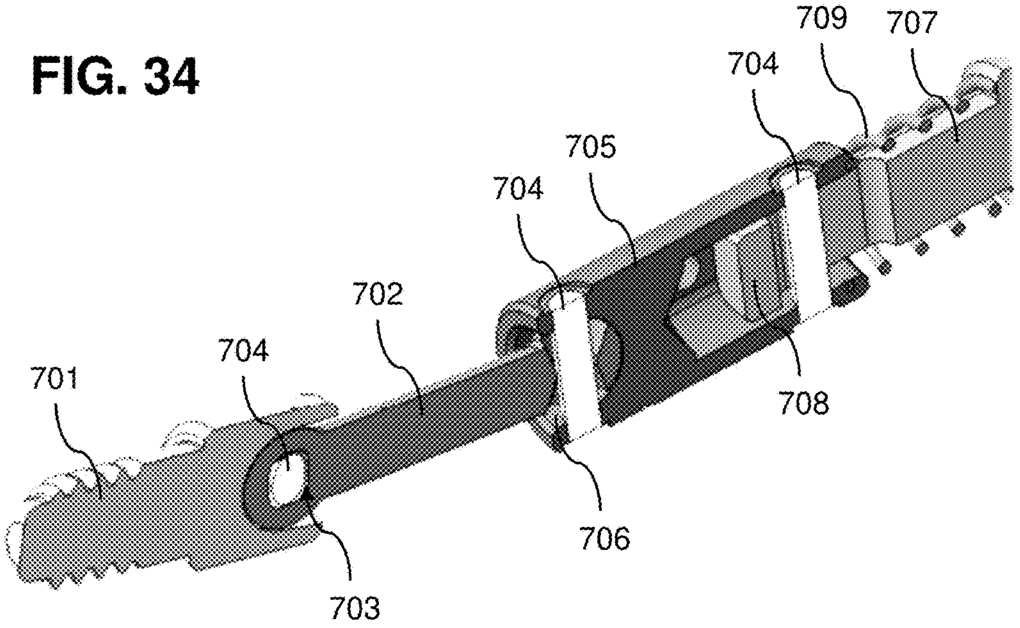
FIG. 34 shows a perspective section view of a portion of a trial inserter in accordance with an embodiment of the invention.

In another embodiment, shown in FIGS. 31-32, distal component 701 couples directly at a proximal end thereof to shaft 707, without an intervening second link 702 and barrel link 705. In this embodiment, distal component 701 is configured to be biased distally by spring 709.

Figure 27:
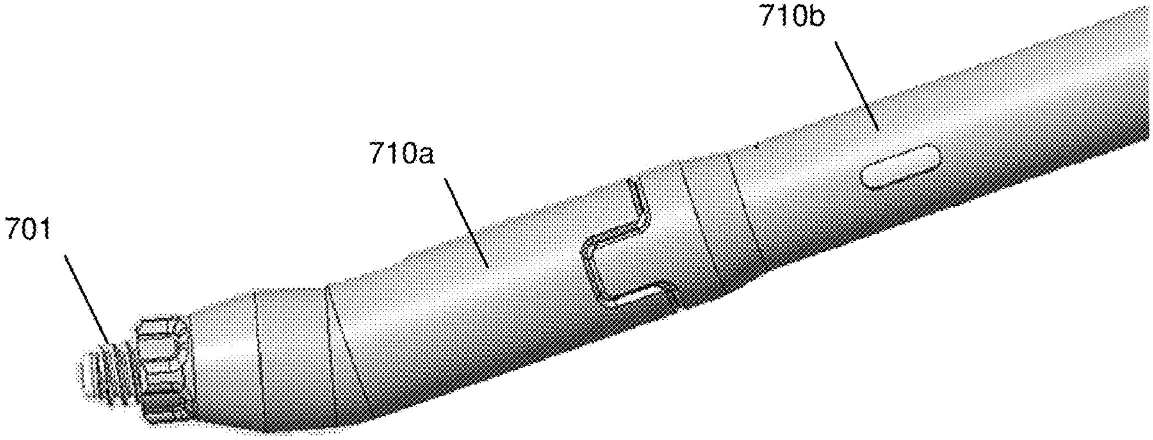
FIGS. 27 and 28 show a side view and a cross sectional view, respectively, of a trial inserter in accordance with an embodiment of the invention.
Figure 28:
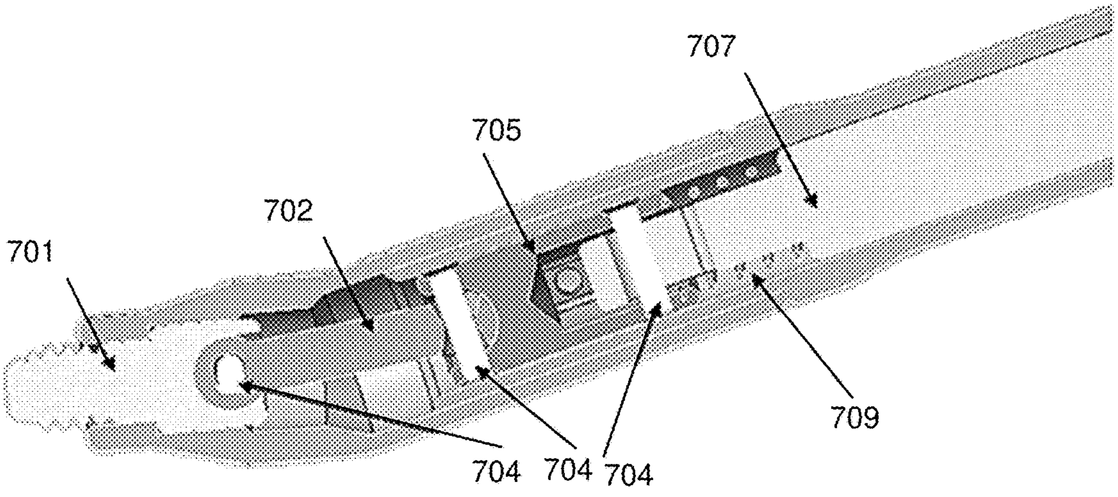
Figure 29:
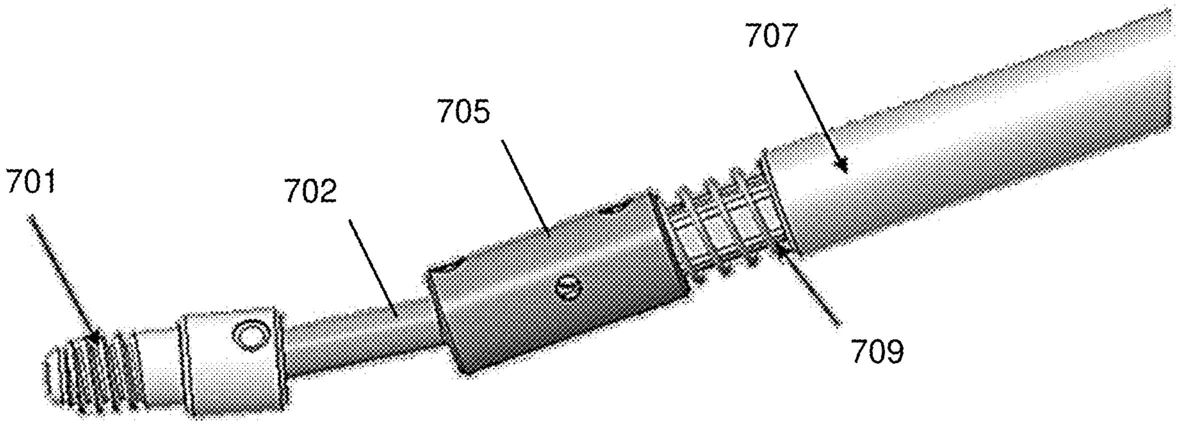
FIG. 29 shows a side view of a trial inserter without the outer shaft present, in accordance with an embodiment of the invention.
Figure 30:
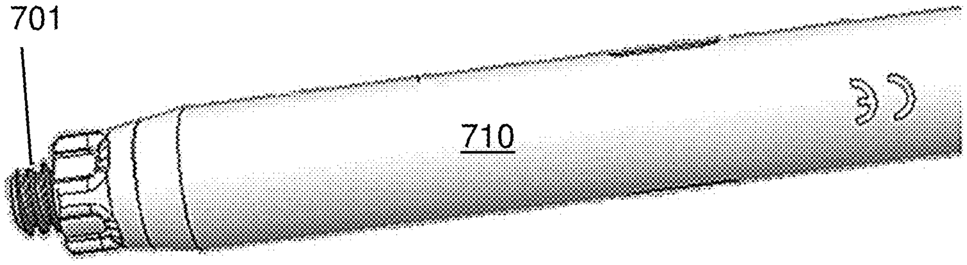
FIG. 30 shows a side view of a trial inserter with an outer shaft in accordance with an embodiment of the invention.

The foregoing components, depicted in FIGS. 27-34, are housed within outer shaft 710, which may be formed of first and second outer shaft portions 710a and 710b (FIG. 27). The distal component 701 is configured to translate into and out of the shaft or housing 710. When the spring loaded and linked inner shaft including 701, 702, 705 is biased outward in a distal direction, as described herein relative to, e.g., FIGS. 33-34, the threads located on the distal end of distal component 701 are configured to readily engage with an implant. The linked inner shaft configuration described herein further provides improved ability to dismantle the device, which may be particularly advantageous for cleaning and sterilization purposes. Similarly, in the embodiment of FIGS. 31-32, the biasing action of spring 709 on distal component 701 places the threads located on the distal end of distal component 701 into position to readily engage with an implant.

In another embodiment for a trial inserter, a distal component is threaded to couple directly to an implant or trial. This distal component link (first link) is rotated to mate through the internal linkage to create the connection. The distal link connects to the main shaft through a square drive feature and slotted pin allowing for translation and torque transmission. The spring in between the distal link and main inner shaft pushes the linkage distally to aid in connection. All of this is housed within the outer shaft. The distal link is pinned to the main shaft capturing the plunger spring between the two components. The distal link can translate into and out of the outer shaft or housing.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated. As used in this specification and the claims, unless otherwise stated, the term "about," "approximately," "generally," and "substantially" refers to variations of less than or equal to +/−1%, +/−2%, +/−3%, +/−4%, +/−5%, +/−6%, +/−7%, +/−8%, +/−9%, +/−10%, +/−11%, +/−12%, +/−14%, +/−15%, +/−16%, +/−17%, +/−18%, +/−19%, or +/−20%, depending on the embodiment. As a further non-limiting example, about 100 millimeters represents a range of 95 millimeters to 105 millimeters, 90 millimeters to 110 millimeters, or 85 millimeters to 115 millimeters, depending on the embodiments.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A spinal implant comprising:
an upper endplate;
a lower endplate;
a central body fixedly placed between the upper and lower endplates, the central body defining a first end, a second end opposing the first end, and at least two sides; and
a plurality of fixation apertures, each defined in part by a solid wall;
wherein the spinal implant defines a fusion aperture between the upper endplate to the lower endplate;

wherein each of the plurality of fixation apertures extends from the second end of the central body to one of the upper endplate or the lower endplate,
wherein at least one of the solid walls includes:
a retaining feature configured to retain a bone screw within one or more of the plurality of fixation apertures; and
a confirmation feature configured to provide tactile feedback to a user when the corresponding bone screw has been fully inserted into the corresponding fixation aperture,
wherein the confirmation feature comprises a triple-lead thread formed integrally as part of the solid wall such that contact between the thread and a ridge of the bone screw provides the tactile feedback to the user.

2. The spinal implant of claim 1,
wherein the retaining feature comprises a deflectable latch having a lip at a proximal end thereof;
wherein the deflectable latch is configured to allow passage of the corresponding bone screw in a first direction through the corresponding fixation aperture and retain the bone screw within the corresponding fixation aperture after a proximal portion of the bone screw has passed the lip.

3. The spinal implant of claim 1, wherein the thread is at a distal portion of a corresponding fixation aperture.

4. The spinal implant of claim 1, further comprising:
an insertion tool engagement feature that is not in contact with the solid walls of the plurality of fixation apertures;
an insertion tool engagement feature in contact with at least one of the solid walls defining a fixation aperture of the plurality of fixation apertures; or
an insertion tool engagement feature located between and in contact with at least two solid walls defining a fixation aperture of the plurality of fixation apertures.

5. The spinal implant of claim 1,
wherein a first fixation aperture of the plurality of the fixation apertures extends from the second end to the upper endplate;
wherein a first lip of a first deflectable latch of the first fixation aperture extends at least towards the upper endplate;
wherein a second fixation aperture of the one or more of the plurality of the fixation apertures extends from the second end to the lower endplate;
wherein a second lip of a second deflectable latch of the second fixation aperture extends at least towards the lower endplate; and
wherein the first deflectable latch or the second deflectable latch is integral to or fixedly attached to the solid wall or the central body.

6. The spinal implant of claim 1,
wherein the solid wall defining each of the plurality of fixation apertures are not in contact with each other;
wherein at least one of the solid walls defining a fixation aperture of the plurality of fixation apertures is in contact with at least one other solid wall defining a different fixation aperture of the plurality of fixation apertures; or
wherein at least one solid wall defining a fixation aperture is in contact with at least one strut of the central body.

7. The spinal implant of claim 1, wherein the spinal implant is made of titanium.

8. The spinal implant of claim 1,
wherein the upper endplate defines a first plurality of pores having a first average pore size;

wherein the lower endplate defines a second plurality of pores having a second average pore size;

wherein the central body defines a third plurality of pores having a third average pore size;

wherein the third average pore size is greater than the first average pore size and the second average pore size.

9. The spinal implant of claim 1, wherein a first fixation aperture of the plurality of fixation apertures extends in a first direction that is tilted from the lower endplate by a first acute angle; and wherein a second fixation aperture of the plurality of fixation apertures extends in a second direction that is tilted from the lower endplate by a second acute angle.

10. The spinal implant of claim 1, wherein the first end comprises a first height shorter than a second height of the second end.

11. A system comprising:

a bone screw; and a spinal implant comprising:

an upper endplate;

a lower endplate;

a central body fixedly placed between the upper and lower endplates, the central body defining a first end, a second end opposing the first end, and at least two sides; and a fixation aperture defined in part by a wall and extending from the second end of the central body to the upper endplate or the lower endplate, wherein the wall includes:

a retaining feature configured to retain the bone screw within the fixation aperture; and a confirmation feature configured to provide tactile feedback to a user when the bone screw has been fully inserted into the fixation aperture, wherein the confirmation feature comprises a triple-lead thread formed integrally as part of the solid wall such that contact between the thread and a ridge of the bone screw provides the tactile feedback to the user.

12. The system of claim 11, wherein the bone screw extends through the fixation aperture and beyond the upper endplate or the lower endplate.

13. The system of claim 12, wherein the retaining feature comprises a deflectable latch having a lip at a proximal end thereof;

wherein the bone screw is retained within the fixation aperture by the deflectable latch;

wherein the bone screw is disposed within the fixation aperture past the lip; and wherein the lip is in contact with and holding a head of the bone screw, thereby resisting the bone screw from leaving the fixation aperture.

14. The system of claim 12, wherein the confirmation feature comprises a thread formed integrally as part of the wall, wherein the bone screw has a proximal portion and a ridge on the proximal portion, and wherein the ridge and the thread are in contact.

15. A system comprising:

a spinal implant comprising:

an upper endplate;

a lower endplate;

a fusion aperture defined between the upper endplate to the lower endplate;

a central body fixedly placed between the upper and lower endplates, the central body defining a first end, a second end opposing the first end, and at least two sides;

a first fixation aperture defined in part by a first wall and extending from the second end of the central body to the upper endplate, the first wall including a first retaining feature and a first confirmation feature;

a second fixation aperture defined in part by a second wall extending from the second end of the central body to the upper endplate, the second wall including a second retaining feature and a second confirmation feature;

a third fixation aperture defined in part by a third wall extending from the second end of the central body to the lower endplate, the third wall including a third retaining feature and a third confirmation feature; and a fourth fixation aperture defined in part by a fourth wall extending from the second end of the central body to the lower endplate, the fourth wall including a fourth retaining feature and a fourth confirmation feature, wherein the first confirmation feature comprises a triple-lead thread formed integrally as part of the solid wall such that contact between the thread and a ridge of the bone screw provides the tactile feedback to the user.

16. The system of claim 15, further comprising:

a first bone screw extending through the first fixation aperture and beyond the upper endplate;

a second bone screw extending through the second fixation aperture and beyond the upper endplate;

a third bone screw extending through the third fixation aperture and beyond the lower endplate; and a fourth bone screw extending through the fourth fixation aperture and beyond the lower endplate.

17. The system of claim 16, wherein the first retaining feature includes a first deflectable latch deflected by and in contact with a first head of the first bone screw;

wherein the second retaining feature includes a second deflectable latch deflected by and in contact with a second head of the second bone screw;

wherein the third retaining feature includes a third deflectable latch deflected by and in contact with a third head of the third bone screw; and wherein the fourth retaining feature includes a fourth deflectable latch deflected by and in contact with a fourth head of the fourth bone screw.

18. The system of claim 15, wherein the first confirmation feature includes a first thread formed integrally as part of the first wall;

wherein the second confirmation feature includes a second thread formed integrally as part of the second wall;

wherein the third confirmation feature includes a third thread formed integrally as part of the third wall;

wherein the fourth confirmation feature includes a fourth thread formed integrally as part of the fourth wall;

wherein the first bone screw has a first ridge on a first proximal portion;

wherein the second bone screw has a second ridge on a second proximal portion;

wherein the third bone screw has a third ridge on a third proximal portion;

wherein the fourth bone screw has a fourth ridge on a fourth proximal portion;

wherein the first ridge is in contact with the first thread;

wherein the second ridge is in contact with the second thread;

wherein the third ridge is in contact with the third thread; and wherein the fourth ridge is in contact with the fourth thread.

* * * * *